United States Patent
Kaiser et al.

(10) Patent No.: US 12,398,142 B2
(45) Date of Patent: Aug. 26, 2025

(54) ABELSON NON-TYROSINE KINASE COMPOUNDS FOR THE TREATMENT OF NEURODEGENERATIVE DISEASES

(71) Applicant: Emory University, Atlanta, GA (US)

(72) Inventors: Thomas Kaiser, Oxford (GB); Zackery Dentmon, East Point, GA (US); Christopher Dalloul, Terre Haute, IN (US); Dennis Liotta, Atlanta, GA (US)

(73) Assignee: Emory University, Atlanta, GA (US)

( * ) Notice: Subject to any disclaimer, the term of this patent is extended or adjusted under 35 U.S.C. 154(b) by 922 days.

(21) Appl. No.: 17/604,744

(22) PCT Filed: Apr. 17, 2020

(86) PCT No.: PCT/US2020/028834
§ 371 (c)(1),
(2) Date: Oct. 18, 2021

(87) PCT Pub. No.: WO2020/214999
PCT Pub. Date: Oct. 22, 2020

(65) Prior Publication Data
US 2022/0177480 A1    Jun. 9, 2022

Related U.S. Application Data

(60) Provisional application No. 62/835,421, filed on Apr. 17, 2019.

(51) Int. Cl.
C07D 487/04    (2006.01)
C07D 519/00    (2006.01)

(52) U.S. Cl.
CPC .......... *C07D 487/04* (2013.01); *C07D 519/00* (2013.01)

(58) Field of Classification Search
CPC .................. C07D 487/04; C07D 519/00
See application file for complete search history.

(56) References Cited

U.S. PATENT DOCUMENTS

| | | |
|---|---|---|
| 2014/0066434 A1 | 3/2014 | Shakespeare |
| 2015/0105377 A1 | 4/2015 | Gozgit |
| 2016/0368917 A1 | 12/2016 | Zou |

FOREIGN PATENT DOCUMENTS

| | | |
|---|---|---|
| WO | 2007075869 | 7/2007 |
| WO | 2013162727 | 10/2013 |

OTHER PUBLICATIONS

Alzheimer's Drug Discovery Foundation, Cognitive Vitality Report, Nilotinib, 2022 (Year: 2022).*
Iclusig® (ponatinib) tablets for oral use Initial U.S. Approval: 2012 HIghlights of Prescribing Information.
Kaiser et al. Accelerated Discovery of Novel Ponatinib Analogs with Improved Properties for the Treatment of Parkinson's Disease, ACS Med. Chem. Lett. 2020, 11, 491-496.
Karuppagounder et al. The c-Abl inhibitor, Nilotinib, protects dopaminergic neurons in a preclinical animal model of Parkinson's disease, Scientific Reports, 2014, 4 : 4874.
Latifi et al. Thrombotic microangiopathy as a cause of cardiovascular toxicity from the BCR-ABL1 tyrosine kinase inhibitor ponatinib, Blood. 2019, 133(14):1597-1606.
Mahul-Mellier et al. c-Abl phosphorylates a-synuclein and regulates its degradation: implication for a-synuclein clearance and contribution to the pathogenesis of Parkinson's disease, Human Molecular Genetics, 2014, vol. 23, No. 11 2858-2879.
Pagan et al. Pharmacokinetics and pharmacodynamics of a single dose Nilotinib in individuals with Parkinson's disease, Pharmacol Res Perspect. 2019;e00470.
Wu et al. c-Abl-p38α signaling plays an important role in MPTP-induced neuronal death, Cell Death and Differentiation (2016) 23, 542-552.

* cited by examiner

*Primary Examiner* — Jeffrey H Murray
*Assistant Examiner* — Kevin S Martin
(74) *Attorney, Agent, or Firm* — Emory Patent Group

(57) ABSTRACT

The present disclosure relates to compounds for the use of treating neurodegenerative diseases and, in particular, to compounds targeting the Abelson non-tyrosine kinase (c-Abl) protein for such treatment. The neurological disorders and conditions include Parkinson's disease, Alzheimer's disease and the like. It also relates to pharmaceutical compositions and methods of treatment of such neurological disorders involving the c-Abl protein kinase.

12 Claims, 12 Drawing Sheets

ABELSON NON-TYROSINE KINASE COMPOUNDS FOR THE TREATMENT OF NEURODEGENERATIVE DISEASES

CROSS-REFERENCE TO RELATED APPLICATIONS

This application is the National Stage of International Application No. PCT/US2020/028834 filed Apr. 17, 2020, which claims the benefit of U.S. Provisional Application No. 62/835,121 filed Apr. 17, 2019. The entirety of each of these applications is hereby incorporated by reference for all purposes.

TECHNICAL FIELD

The present disclosure relates to compounds for the use of treating neurodegenerative diseases and, in particular, to compounds targeting the Abelson non-tyrosine kinase (c-Abl) protein for such treatment. The neurological disorders and conditions include Parkinson's disease, Alzheimer's disease and the like. It also relates to pharmaceutical compositions and methods of treatment of such neurological disorders involving the c-Abl protein kinase.

BACKGROUND

Neurodegenerative disease, a category which includes Parkinson's disease (PD) and Alzheimer's disease (AD), represents a significant healthcare burden that is expected to increase as lifespans are prolonged worldwide (Elbaz, A. et al., Revue Neurologique 2016, 172, 14-16; Wyss-Coray, T., Nature 2016, 539, 180-186.). A 2015 United Nations report on world population aging anticipates a doubling of the number of people aged 60 years old or older over the next 35 years. This demographic is the most at risk for developing neurodegenerative disease (World Population Ageing 2015 (ST/ESA/SER.A/390). United Nations: New York, NY, 2015). PD is the second most common neurodegenerative disease, affecting 2-3% of those over 65 years of age (Poewe, W. et al. Nature Rev. Disease Primers 2017, 3, 17013.). The classic motor symptoms of PD include bradykinesia, postural instability, resting tremor and muscle stiffness. Additionally, there is significant disability for the patient in that dementia, dysphagia, insomnia and loss of smell frequently develop as well (Chaudhuri, K. R. et al. Lancet Neurol. 2009, 8, 464-474.), with cognitive and behavioral problems developing in later stages of the disease. These non-motor symptoms are a key determinant of the quality of life in PD patients and are gaining recognition as important aspects to consider in therapeutic development (Chaudhuri, K. R. et al. Lancet Neurol. 2009, 8, 464-474; Parkinson's Disease: National Clinical Guideline for Diagnosis and Management in Primary and Secondary Care. Royal College of Physicians: London, UK, 2006; Vol. 35.).

The underlying pathogenesis of PD is a complex process. A key component of the disease process is chronic neurodegeneration due to selective and progressive loss of dopaminergic neurons in the substantia nigra pars compacta (Benarroch, E. E. et al., Mayo Clinic Medical Neurosciences: Organized by Neurologic System and Level. 6th ed.; Oxford University Press: New York, NY, 2018). An additional histopathological feature of PD is the intracellular accumulation of α-synuclein and the subsequent formation of Lewy bodies in the brainstem and olfactory system. However, neither Lewy body formation nor dopaminergic neuron loss of the substantia nigra are unique to PD (Dickson, D. W. et al., Lancet Neurol. 2009, 8, 1150-1157.). It is the combination of these two histopathological features which results in PD (Dickson, D. W. et al., Lancet Neurol. 2009, 8, 1150-1157; Braak, H. et al., Neurobiol. Aging 2003, 24, 197-211.).

Current therapy for PD is entirely focused on symptomatic relief, such as dopamine agonists or levodopa working to alleviate motor symptoms, and there are severe side effects associated with most of the first line agents in clinical use (Poewe, W. et al., Curr. Opin. Neurol. 2012, 25, 448-459). Dyskineasea, exacerbation of insomnia, movement freezing and dose failure are common consequences of L-DOPA/carbidopa therapy (Jankovic, J. et al., Curr. Opin. Neurol. 2012, 25, 433-447.).

There are no current treatments able to slow, prevent, or reverse PD (Zhou, Z. H. et al., Neurol Sci 2017, 38, 547). However, new insights into the pathological mechanisms has provided a novel tactic in approaching PD drug development. Work in both animal models of PD and in post-mortem analysis of human tissue affected by PD has revealed a role of oxidative stress in dopaminergic neurons as a key pathogenic step (Wyss-Coray, T., Nature 2016, 539, 180-186; Zhang, Y et al., Neurobiol. Disease 2000, 7, 240-250). One of the key links between oxidative stress and neurodegeneration has been the Abelson non-tyrosine kinase (c-Abl), a kinase historically associated with the BCR-Abl fusion gene in certain leukemias. Recent work has linked aberrations in c-Abl activity in response to oxidative stress to the pathogenesis of neurodegeneration including AD and PD (Li, B., Cell Cycle 2005, 4, 201-203; Schlatterer, S. D. et al., J. Mol. Neurosci. 2011, 45, 445-452; Imam, S. Z. et al., J. Neurosci. 2011, 31, 157-163; Ko, H. S. et al., PNAS 2010, 107, 16691-16696; Mahul-Mellier, A.-L. et al., Human Mol. Gen. 2014, 23, 2858-2879).

c-Abl has been implicated in a wide variety of natural processes including cell differentiation, cell division, cell adhesion, and oxidative stress responses. It already has clinical significance; mutations of the ABL1 gene are oncogenic and primarily associated with chronic myelogenous leukemia (CML). The translocation of ABL1 within the breakpoint cluster region gene (BCR) on chromosome 22 results in the oncogenic fusion protein, BCR-ABL, allowing it to proliferate without being regulated by cytokines (Heisterkamp, N. et al., J. Hematol Pathol 1991, 5, 1). Treatment for CML is possible by inhibition of the BCR-ABL fusion protein through various marketed small molecules shown below.

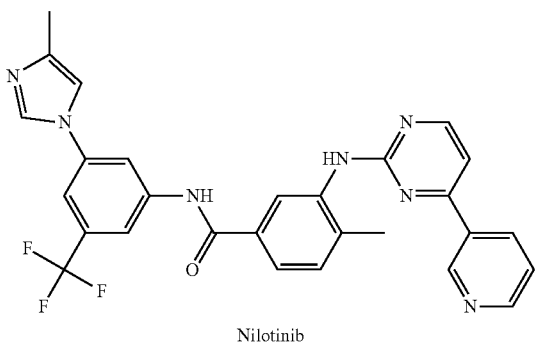

Nilotinib

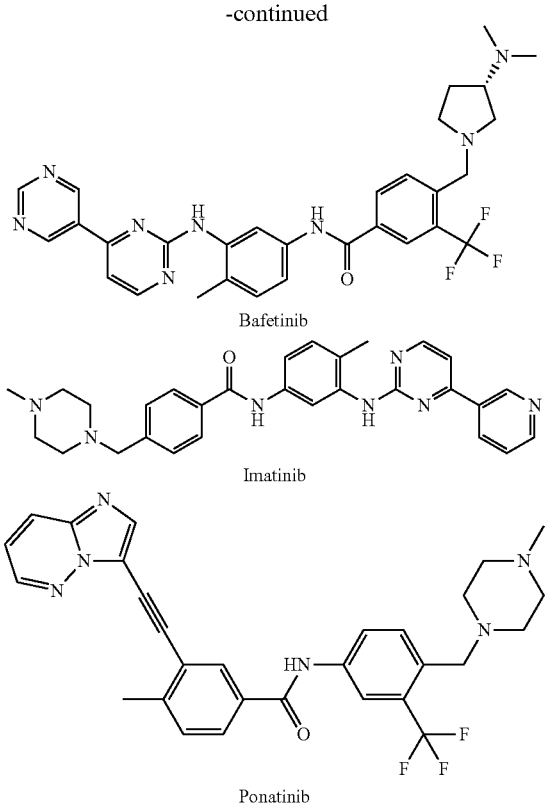

Bafetinib

Imatinib

Ponatinib c-Abl has been demonstrated to play a role in the reduction of dopamine levels in the brain. One of the hallmarks of PD is the loss of dopamine-producing neurons in the substantia nigra; low dopamine levels result in the development of impaired motor function. Inhibition of c-Abl has protected against the reduction in dopamine in PD mice models (MTPT and α-synuclein-induced) (Pagan, F. et al., J Parkinsons Dis 2016, 6, 503; Hebron, M. L. et al., Hum Mol Genet 2013, 22, 3315; Imam, S. Z. et al., PLoS One 2013, 8, e65129; Karuppagounder, S. S. et al., Sci Rep 2014, 4, 4874).

The Parkin protein is critical in mitochondrial quality control, amplifying cascades to induce rapid mitophagy (Lazarou, M. et al., Nature 2015, 524, 309). c-Abl activation and subsequent phosphorylation of parkin results in inhibition of the ubiquitin ligase activity of parkin and results in the accumulation of toxic parkin substrates including parkin interacting substrate (PARIS) and aminoacyl tRNA synthetase complex-interacting multifunctional protein 2 (AIMP2) (Shin, J.-H. et al., Cell 2011, 144, 689-702; Lee, Y et al., Nature Neurosci. 2013, 16, 1392-1400). Bolstering the importance of PARIS and AIMP2 in the pathogenesis of PD is the finding that both PARIS and AIMP2 accumulate in familial PD resulting from parkin mutations and in MPTP toxin mouse models of PD (Shin, J.-H. et al., Cell 2011, 144, 689-702; Lee, Y et al., Nature Neurosci. 2013, 16, 1392-1400). This biological insight led to several groups exploring the Parkinson's disease treatment opportunities for approved BCR-Abl inhibitors also known to inhibit c-Abl like imatinib and nilotinib. Imatinib was found to restore parkin ubiquitin ligase activity and reduce PARIS and AIMP2 levels in the MPTP mouse model (Imam, S. Z. et al., J. Neurosci. 2011, 31, 157-163; Ko, H. S. et al., PNAS 2010, 107, 16691-16696).

Nilotinib, a marketed c-Abl inhibitor for the treatment of CML, was also found to protect against MPTP-induced dopaminergic deficits, and nilotinib administration in this model reversed the loss of dopamine neurons in this model, a result known to lead to improved motor behavior (Karuppagounder, S. S. et al., Sci. Rep. 2014, 4, 4874; Hebron, M. L. et al., Human Mol. Gen. 2013, 22, 3315-3328). In c-Abl knockout mice, the loss of these neurons was also significantly prevented in PD mice models (Ko, H. S. et al., Proc Natl Acad Sci USA 2010, 107, 16691; Wu, R. et al., Z. Cell Death Differ 2016, 23, 542). Nilotinib also facilitates α-synuclein protein degradation via autophagy (Mahul-Mellier, A. L. et al., Hum Mol Genet 2014, 23, 2858). Nilotinib has been suggested to improve motor and cognitive outcomes in a 12-patient non-randomized trial conducted by Georgetown University (Pagan, F. et al., J. Parkinson's Disease 2016, 6, 503-517). A follow-up study evaluating the pharmacokinetics and pharmacodynamics of nilotinib in PD patients found that nilotinib as a 200 mg single dose was capable of increasing cerebrospinal fluid concentrations of metabolites of dopamine (Pagan, F. L. et al., Pharmacol. Res. Perspectives 2019, e00470). A phase II trial evaluating nilotinib in PD is currently underway (NCT02954978). However, there are significant limitations to nilotinib administration for a PD application that needs to be taken chronically. Nilotinib is known to be a potent inhibitor of hERG, a potassium channel which generates the repolarization current in the cardiac action potential. Inhibition of this repolarization process is known to lead to prolongation of the QT interval, which can progress to torsades de points and cardiac arrest. Thus, nilotinib and other c-Abl inhibitors were only intended for short-term therapy and carry black-box warnings for QT prolongation or cardiotoxicity as a result of potent hERG inhibition (nilotinib's hERG $IC_{50}$=660 nM) (Weisberg, E. et al., Cancer Cell 2005, 7, 129).

Ariad Pharmaceuticals compound, ponatinib treats patients with chronic myeloid leukemia and inter alia c-Abl (see patent applications WO2013/162727 and WO 2007/075869). However, this compound has a black box warning for vascular occlusion, heart failure and hepatotoxicity (see Latifi et al., Blood, 2018, 10, 881557; Rivera et al., Blood, 2014, 124, 1783).

Thus, there is a need for new compounds for the targeting c-abl for treating these neurological conditions that alleviate the abovementioned problems, to some extent at least.

SUMMARY

In accordance with an embodiment of the present disclosure there is provided a compound of Formula (I) or salt thereof, Formula (I)

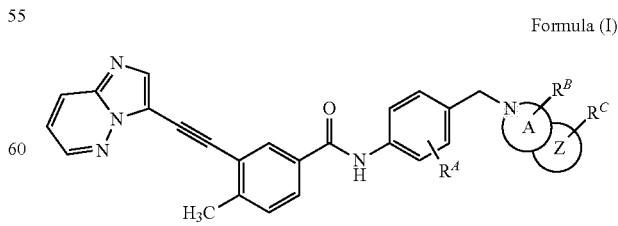

wherein $R^A$ is a halogen or a $C_2$-$C_4$ alkyl, which may be saturated or unsaturated, branched or cyclic and $R^A$ is optionally substituted with $R^{10}$;

$R^B$ and $R^C$ are individually and independently selected from a H, hydroxyl, a $C_2$-$C_4$ alkyl, which may be saturated or unsaturated, branched or cyclic, halogen, nitro, cyano, hydroxy, amino, formyl, carbamoyl, alkoxy, acetyl, carbocyclyl, aryl, or heterocyclyl and $R^B$ and $R^C$ are each optionally substituted with $R^{10}$;

Ring Y is a 5 or 6 membered carbocyclyl, aryl, or heterocyclyl;

Ring Z is a 5 or 6 membered carbocyclyl, aryl, or heterocyclyl or is absent; and $R^{10}$ is a halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Further features provide for $R^4$ to be a halogen or a $C_3$-$C_4$ cycloalkyl; for $R^B$ to be H, $C_2$ to $C_4$ alkyl or alkoxy and $R^C$ to be H, hydroxyl, a $C_2$-$C_4$ alkyl or halogen; for Ring Y to be a 5 or 6 membered aryl, or heterocyclyl and for Ring Z to be a 5 or 6 membered aryl, or heterocyclyl or absent.

Still further features provide for Ring Y to be:

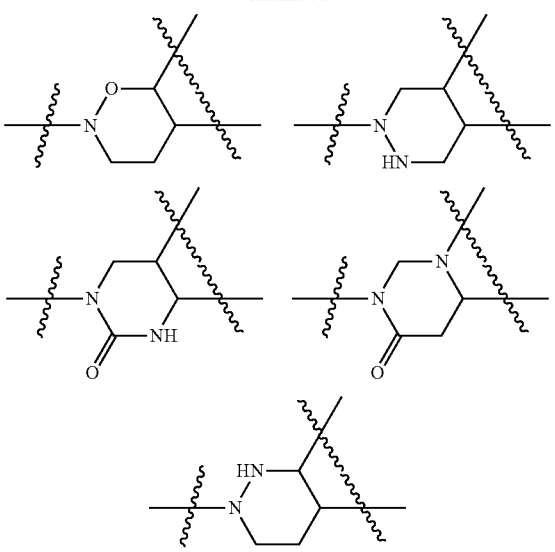

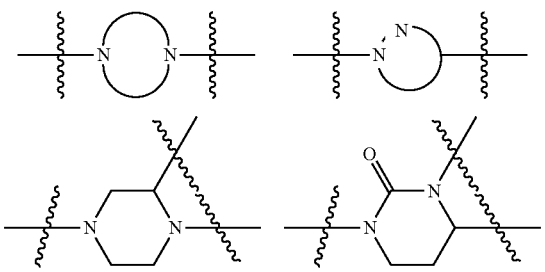

and for Ring Z to selected from:

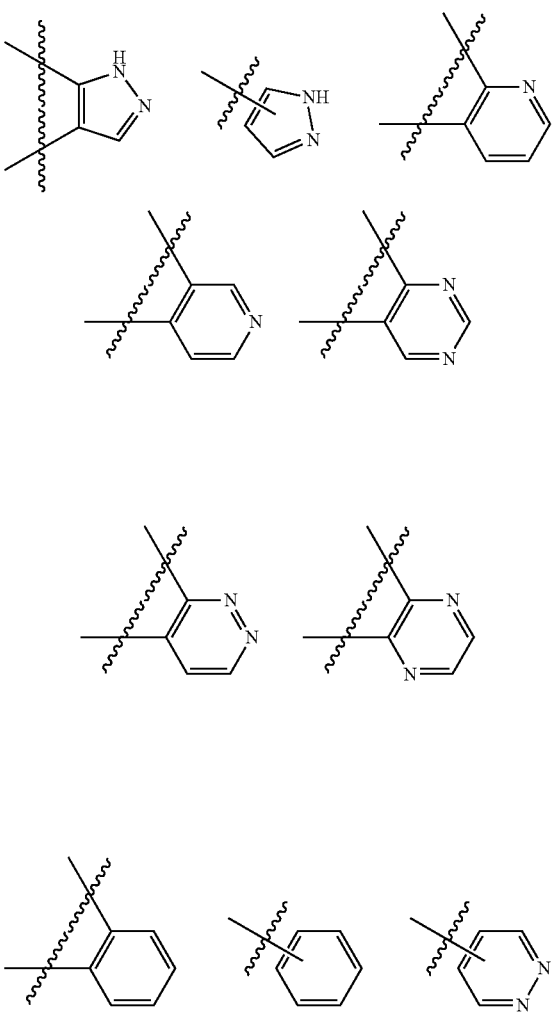

-continued

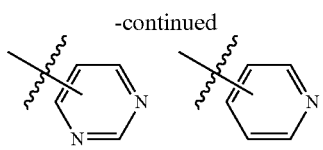

Exemplary compounds of Formula (I) include:

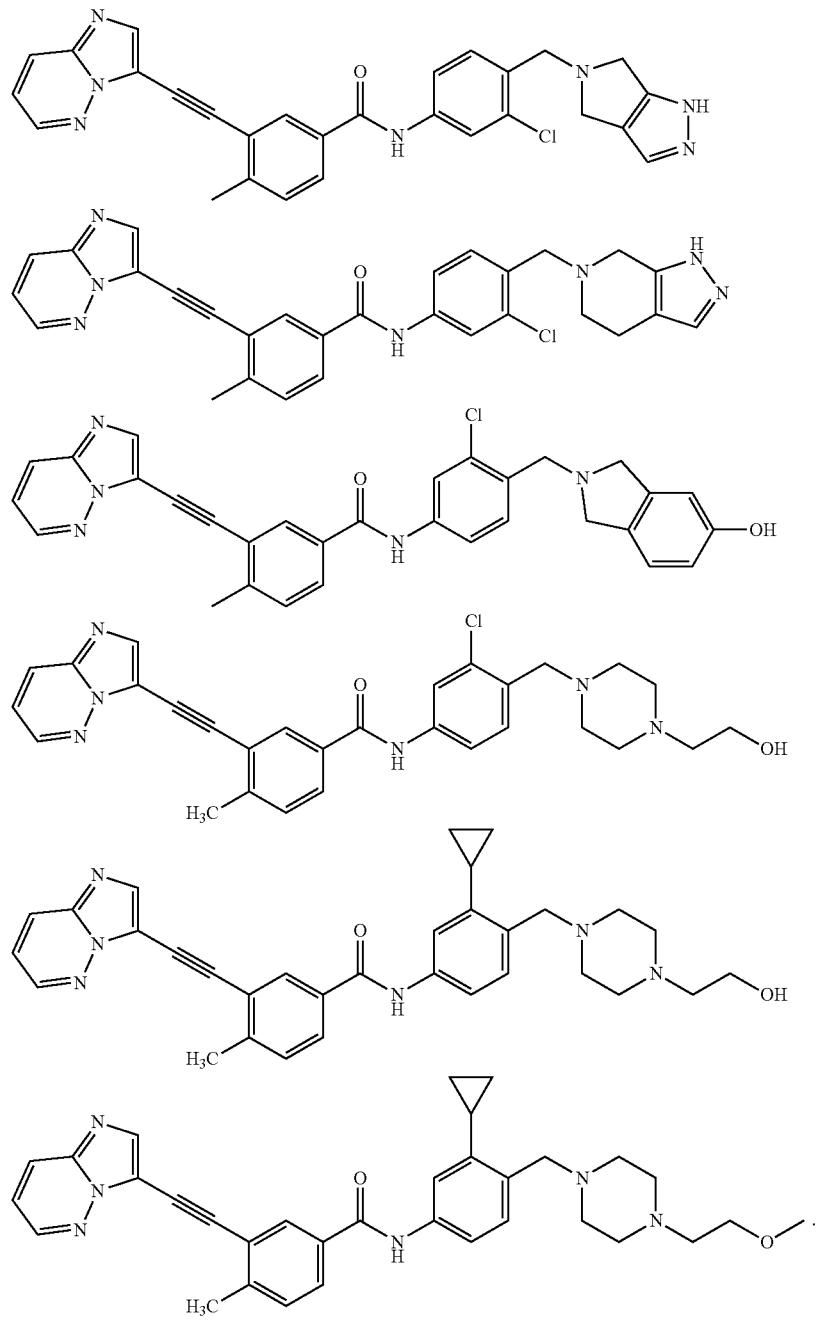

Treatment of neurological disorders include providing neuroprotection, preventing neurodegeneration, treating Parkinson's disease, Alzheimer's disease and the like.

In certain embodiments, the disclosure contemplates derivatives of compounds disclosed herein such as those containing one or more, the same or different, substituents.

In still another embodiment there is provided a pharmaceutical composition comprising a compound of Formula (I) or salts thereof and a pharmaceutically acceptable excipient. In certain embodiments, the pharmaceutical composition is in the form of a tablet, capsule, pill, gel, granules, aerosol, or aqueous buffer, such as a saline or phosphate buffer, or a nanoparticle formulation, emulsion, liposome, etc. The phar- In another embodiment there is provided a method of treating a variety of neurological disorders in a subject in need thereof, the method comprising administering an effective amount of the compound of Formula (I) or salts thereof to the subject.

maceutical composition may also include one or more further active agents or may be administered in combination with one or more such active agent.

In yet further embodiments, there is provided methods for preparing the compounds of Formula (I) or salts thereof comprising mixing one or more starting materials with reagents under conditions such that the products are formed.

In yet further embodiments, there is provided uses of compounds of Formula (I) or salts thereof in the production of a medicament for use in treating a neurological disorder.

DETAILED DESCRIPTION

Terms

Figure 1:
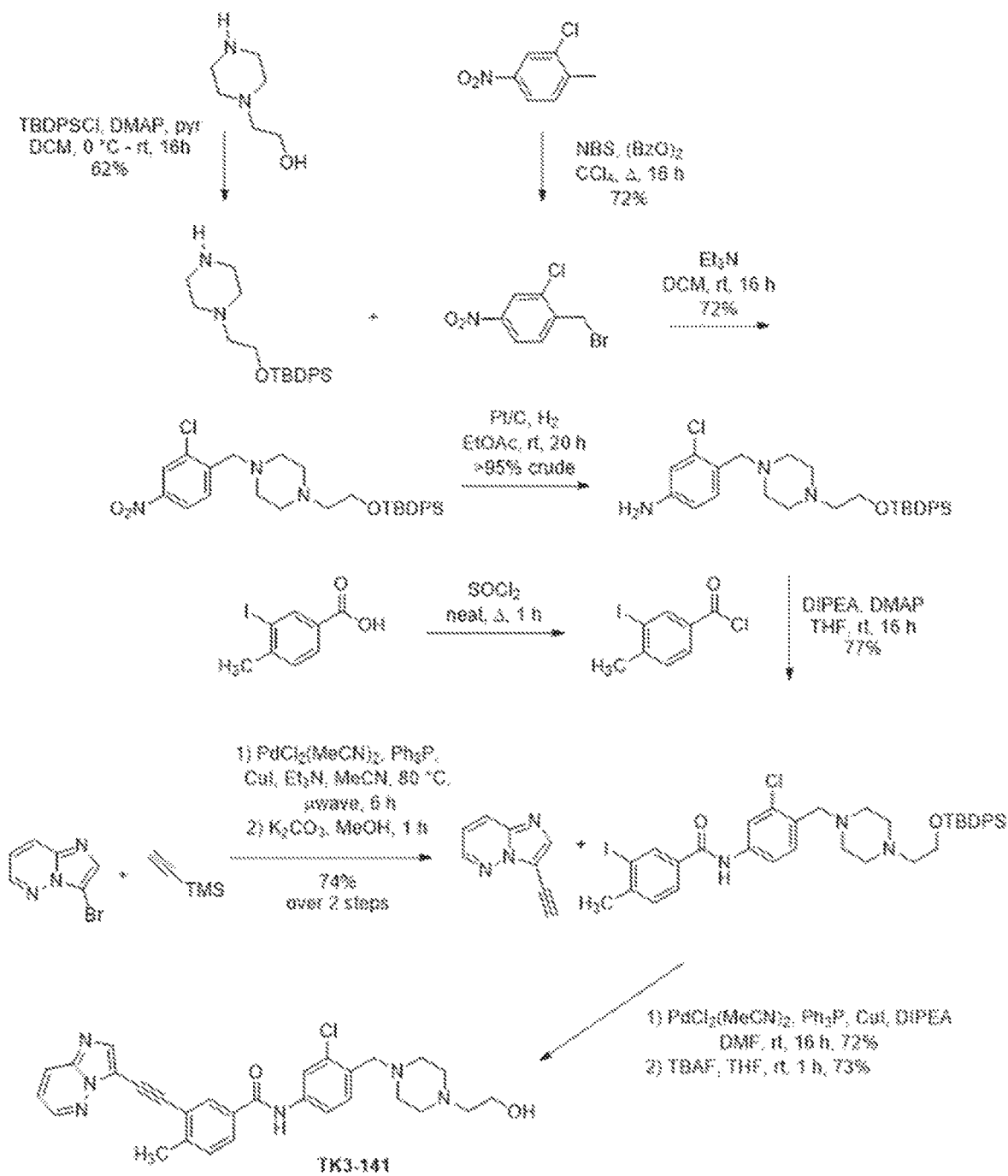
FIG. 1 shows a reaction scheme for the synthesis of exemplary compound TK3-141.
Figure 2:
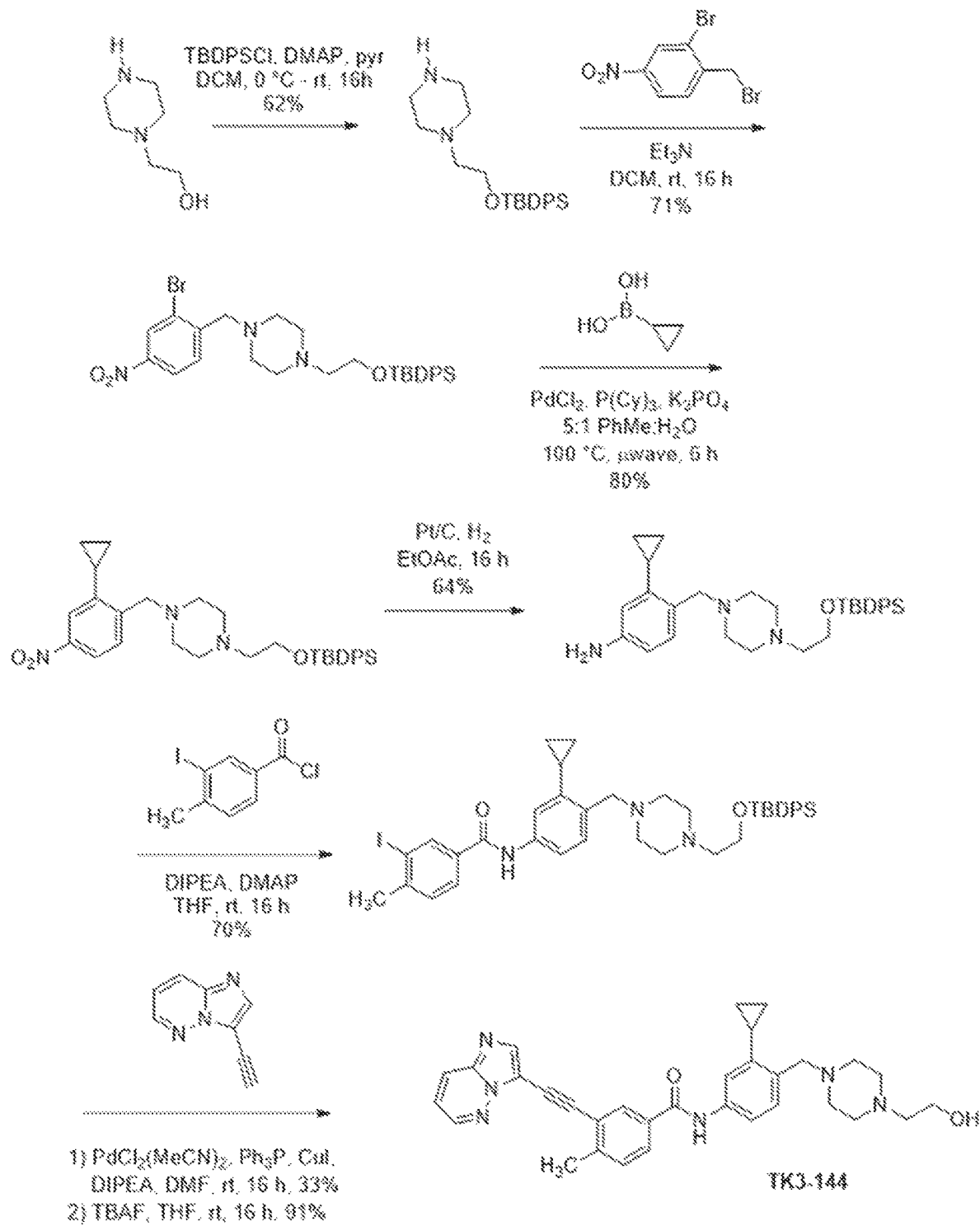
FIG. 2 shows a reaction scheme for the synthesis of exemplary compound TK3-144.
Figure 3:
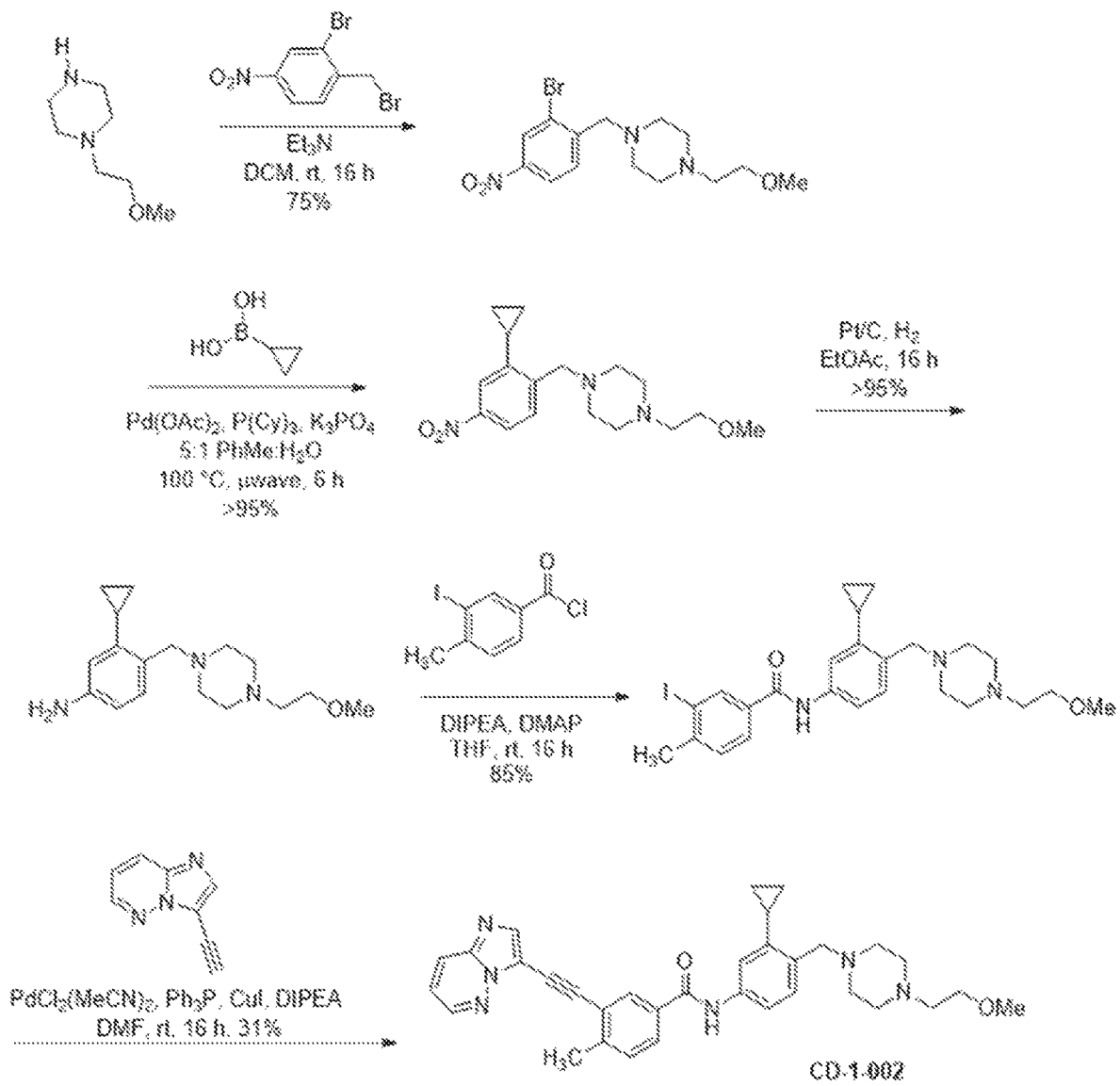
FIG. 3 shows a reaction scheme for the synthesis of exemplary compound CD-1-002.
Figure 4:
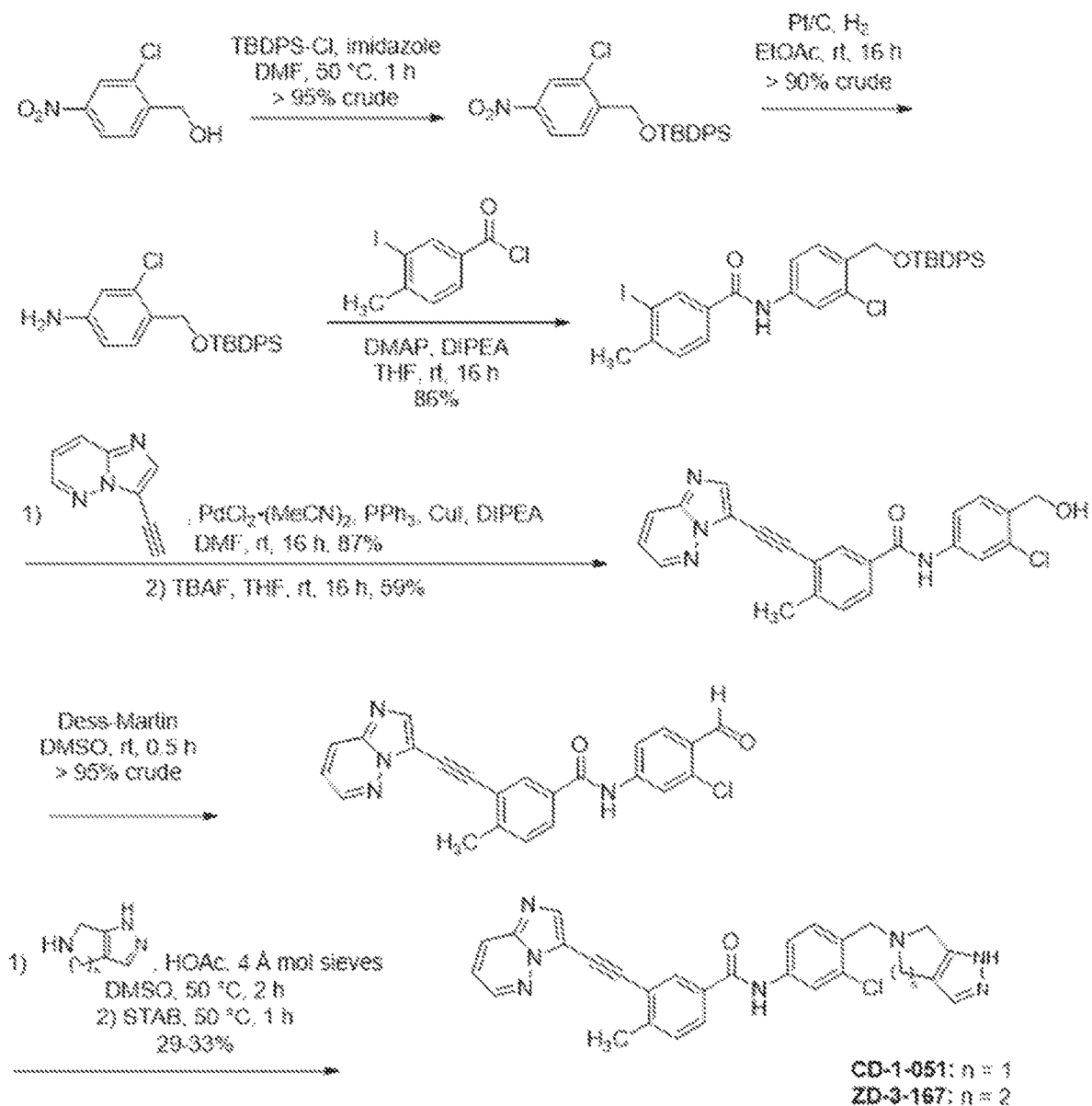
FIG. 4 shows a reaction scheme for the synthesis of exemplary compound CD-1-051 and ZA-3-167.
Figure 5:
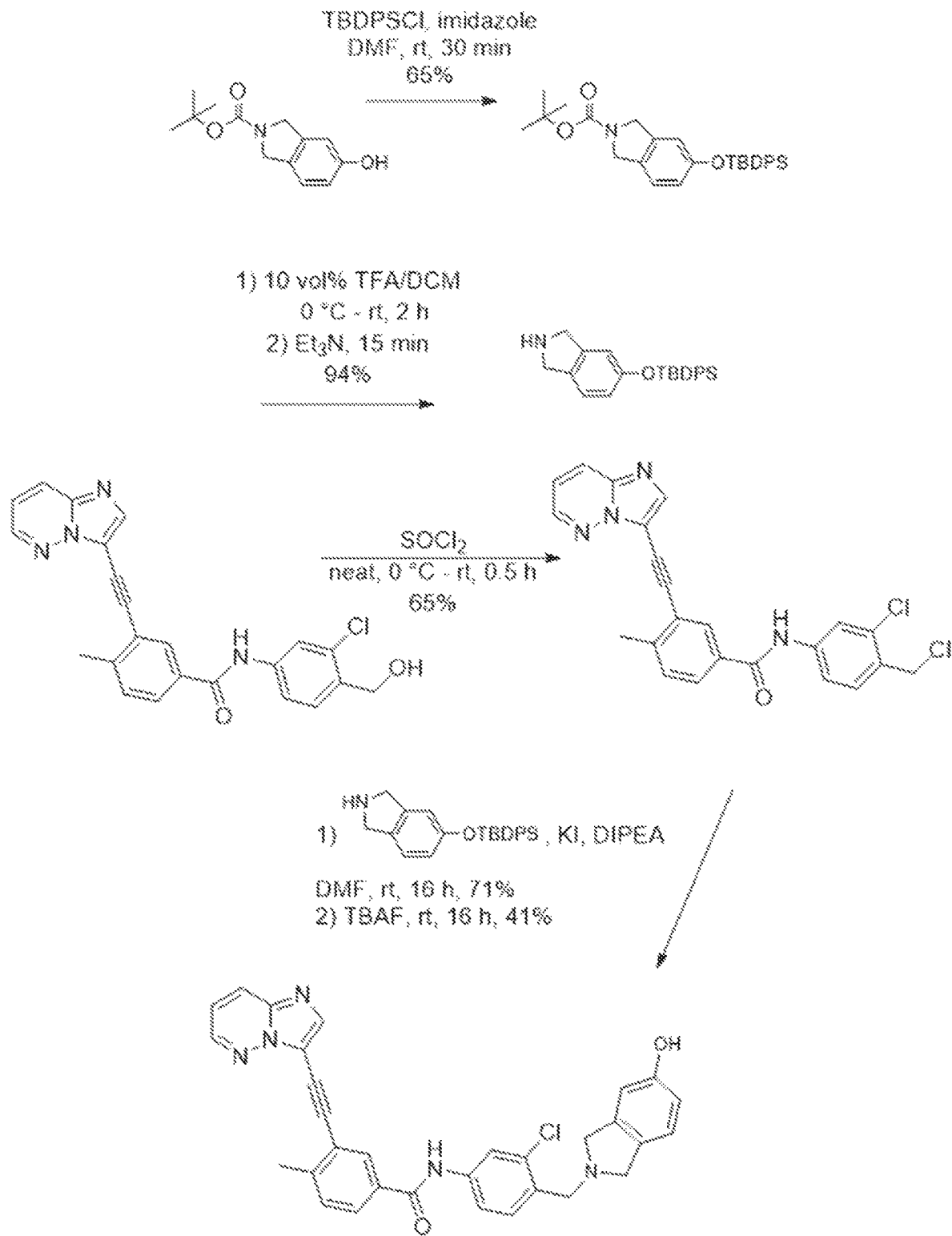
FIG. 5 shows a reaction scheme for the synthesis of exemplary compound CD-1-067.

Before the present disclosure is described in greater detail, it is to be understood that this disclosure is not limited to embodiments described, and as such may, of course, vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

To the extent that any chemical formulas reported herein contain one or more chiral centers, the formulas are intended to encompass all stable stereoisomers, enantiomers, and diastereomers. It is also understood that formulas encompass all tautomeric forms.

It must be noted that, as used in the specification and the appended claims, the singular forms "a", "an", and "the" include plural referents unless the context clearly dictates otherwise.

"Subject" refers any animal, preferably a human patient, livestock, mouse model or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, "alkyl" means a noncyclic straight chain or branched, unsaturated or saturated hydrocarbon such as those containing from 1 to 20 carbon atoms. In certain embodiments, any "alkyl" disclosed herein may be a lower alkyl and a higher alkyl or any of the specific alkyl groups reported in this section. A "lower alkyl" refers to unsaturated or saturated hydrocarbons having 1 to 6 carbon atoms or 1 to 4 carbon atoms and a "higher alkyl" refers to unsaturated or saturated hydrocarbon having 6 or more carbon atoms. A "$C_8$-$C_{18}$" refers to an alkyl containing 8 to 18 carbon atoms. Likewise, a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, hexadecyl, dodecyl, tetradecyl, izosonyl, octadecyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like. Carbocyclyls include cycloalkyls and cycloalkenyls.

"Heterocarbocycles" or "heterocarbocyclyl" groups are carbocycles which contain from 1 to 4 heteroatoms independently selected from nitrogen, phosphorous, oxygen and sulphur which may be saturated or unsaturated (but not aromatic), monocyclic or polycyclic, and wherein the nitrogen and sulphur heteroatoms may be optionally oxidized (e.g. —S(O)—, —SO$_2$—, —N(O)—), and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

The terms "cycloalkyl" and "cycloalkenyl" refer to mono-, bi-, or tri homocyclic ring groups of 3 to 15 carbon atoms which are, respectively, fully saturated and partially unsaturated.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

The term "substituted" refers to a molecule wherein at least one hydrogen atom is replaced with a substituent. When substituted, one or more of the groups are "substituents". The molecule may be multiply substituted. In the case of an oxo substituent (═O), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO$_2$Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted", as used herein, means that substitution is optional and therefore it is possible for the designated atom to be unsubstituted.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optionally has one or more, the same or different, substitutions. Derivatives may be prepared by any variety of synthetic methods or appropriate adaptations presented in synthetic or organic chemistry text books, such as those provided in "March's Advanced Organic Chemistry: Reactions, Mechanisms, and Structure", Wiley, 6th Edition (2007) Michael B. Smith or "Domino Reactions in Organic Synthesis", Wiley (2006) Lutz F. Tietze, hereby incorporated by reference.

Pharmaceutical Compositions Including the Compounds

Mammals, and specifically humans, suffering from neurodegenerative disorders involving the c-abl kinase, or any of the above-described conditions can be treated by either targeted or systemic administration, via oral, inhalation, topical, trans- or sub-mucosal, subcutaneous, parenteral, intramuscular, intravenous or transdermal administration of a composition comprising an effective amount of the compounds described herein or a pharmaceutically acceptable salt, ester or prodrug thereof, optionally in a pharmaceutically acceptable carrier. The compounds or composition is typically administered by oral administration. Alternatively, compounds can be administered by inhalation. In another embodiment, the compound is administered transdermally (for example via a slow release patch), or topically. In yet another embodiment, the compound is administered subcutaneously, intravenously, intraperitoneally, intramuscularly, parenterally, or submucosally. In any of these embodiments, the compound is administered in an effective dosage range to treat the target condition.

In one embodiment, compounds of the present invention are administered orally. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

When the compound is administered orally in the form of a dosage, tablets, pills, capsules, troches and the like, these can contain any of the following ingredients, or compounds of a similar nature: a binder (such as microcrystalline cellulose, gum tragacanth or gelatin); an excipient (such as starch or lactose), a disintegrating agent (such as alginic acid, Primogel, or corn starch); a lubricant (such as magnesium stearate or Sterotes); a glidant (such as colloidal silicon dioxide); a sweetening agent (such as sucrose or saccharin); and/or a flavoring agent (such as peppermint, methyl salicylate, or orange flavoring). When the dosage unit form is a capsule, it can contain, in addition to material of the above type, a liquid carrier (such as a fatty oil). In addition, dosage unit forms can contain various other materials which modify the physical form of the dosage unit, for example, coatings of sugar, shellac, or other enteric agents. The compound or its salts can also be administered orally as a component of an elixir, suspension, syrup, wafer, chewing gum or the like. A syrup may contain, in addition to the active compounds, a sweetening agent (such as sucrose, saccharine, etc.) and preservatives, dyes and colorings and flavors.

The compounds of the invention may also be administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate. In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or as pressure such as the dry-powder inhaler.

A parenteral preparation can be enclosed in ampoules, disposable syringes or multiple dose vials made of glass or plastic.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

If administered intravenously, carriers can be physiological saline, bacteriostatic water, Cremophor EL™ (BASF, Parsippany, NJ) or phosphate buffered saline (PBS). In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Dosing

The compound is administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single oral dosage once a day. The active compound is included in the pharmaceutically acceptable carrier or diluent in an amount sufficient to deliver to a patient a therapeutic amount of compound in vivo in the absence of serious toxic effects. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

Typical systemic dosages for the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as single daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Treatment

The compound can also be mixed with other active materials which do not impair the desired action, or with materials that supplement the desired action. The active compounds can be administered in conjunction, i.e. combination or alternation, with other medications used in the treatment or prevention of Parkinson's disease and other neurologic events or neurodegeneration involving the c-Abl kinase. In another embodiment, the compounds can be administered in conjunction (combination or alternation) with other medications used in treatment or prophylaxis of inflammatory conditions. In certain embodiments, the combination can be synergistic although in other embodiments the combination is not synergistic.

Methods of Treatment Using the Compounds

In one embodiment, the compounds are used in a method of treatment or prophylaxis of Parkinson's disease and other neurologic events, neurocognitive disorders, tardive dyskinesia, motor disorders, mood disorders or neurodegeneration involving c-Abl kinase comprising administering to a host in need thereof an effective amount of a compound described herein, optionally in a pharmaceutically acceptable carrier. The compounds can be administered, alone or in a pharmaceutically acceptable carrier, to a patient suffering from, or at risk of developing the various disorders, to treat, prevent, or reduce the symptoms of or cognitive deficits associated with the various disorders.

The compounds described herein can also generally be used to treat neurologic events and neurodegeneration, whether or not such neurologic event or neurodegeneration is associated with c-Abl kinase.

Further, compounds selected according to the methods or processes described herein can be used prophylactically to prevent or protect against such diseases or neurological conditions, such as those described herein.

In all these embodiments, the methods involve administering a compound of Formula (I) or a pharmaceutically acceptable salt, ester, or derivative thereof, or a pharmaceutical composition thereof.

Examples

The present disclosure will now be described in more detail with reference to the following non-limiting examples. It should be noted that the particular assays used in the examples section are designed to provide an indication of activity.

Experimental Procedures

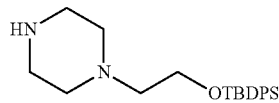

tert-butyl-diphenyl-(2-piperazin-1-ylethoxy)silane 2-(piperazin-1-yl)ethanol (15 g, 115.2 mmol) was dissolved in DCM (520 ml) under argon, and pyridine (14 ml, 172.8 mmol) followed by DMAP (1.41 g, 11.5 mmol) were added. The reaction was cooled to 0° C. and tert-butylchlorodiphenylsilane (36 ml, 138.3 mmol) was added to the solution. The reaction mixture was allowed to warm to ambient temperature and stirred overnight. The next day, the reaction mixture was concentrated under reduced pressure and the concentrate was purified by column chromatography (0-10% MeOH in DCM) to give the title product (26.4 g, 62% yield).

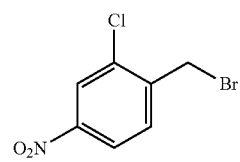

1-(bromomethyl)-2-chloro-4-nitro-benzene: To a stirred, heated (80° C.) solution of 2-chloro-4-nitrotoluene (7.9424 g, 46.3 mmol) and N-bromosuccinimide (8.24 g, 46.2 mmol) in anhydrous carbon tetrachloride (12 mL) was added, under Ar, benzoyl peroxide (224 mg, 0.69 mmol, 75% pure), and the resulting mixture was heated to reflux overnight. After cooling to room temperature, the mixture was diluted with Et$_2$O (100 mL), water was added (50 mL), and the phases were separated. The aqueous layer was extracted with Et$_2$O (2×100 mL), and the combined organic phases were dried with Na$_2$SO$_4$. After filtration and evaporation of the solvent, the residue was purified by column chromatography (0-10% EtOAc in Hexanes) to give pure 2-chloro-4-nitrobenzyl bromide as a yellow oil (8.3 g, 72% yield).

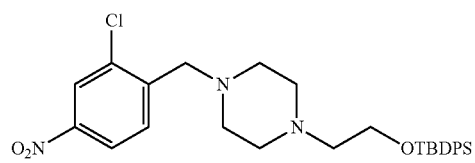

Tert-butyl-[2-[4-[(2-chloro-4-nitro-phenyl)methyl]piperazin-1-yl]ethoxy]-diphenyl-silane: To a solution of 2-chloro-5-nitro-bromomethyl benzene (2.04 g, 8.14 mmol) in CH$_2$Cl$_2$ (8.1 mL) was added Et$_3$N (1.13 mL, 8.14 mmol) and tert-butyl-diphenyl-(2-piperazin-1-ylethoxy)silane (3 g, 8.14 mmol) under argon. The reaction was allowed to stir at ambient temperature overnight. A saturated aqueous solution of NaHCO$_3$ was added (10 mL) and diluted with 15 mL of water, and the mixture was extracted with CH$_2$Cl$_2$ (3×75 mL). The combined organic layer was dried over Na$_2$SO$_4$, filtered, concentrated, and the resulting residue was purified by silica gel chromatography (0-20% EtOAc in Hexanes) to afford the product as an orange oil (3.17 g, 72% yield).

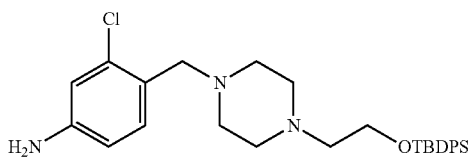

4-[[4-[2-[tert-butyl(diphenyl)silyl]oxyethyl]piperazin-1-yl]methyl]-3-chloro-aniline: A solution of tert-butyl-[2-[4-[(2-chloro-4-nitro-phenyl)methyl]piperazin-1-yl]ethoxy]-diphenyl-silane (3.17 g, 5.89 mmol) in ethyl acetate (125 ml) was catalytically hydrogenated over 5% platinum on carbon (1.011 g, 0.2592 mmol) under a balloon of H₂ gas at ambient temperature overnight. The reaction mixture was filtered through celite, and the filtrate was concentrated to afford the desired product which was used as-is its next step.

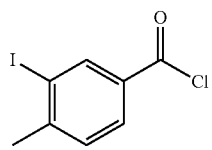

3-iodo-4-methyl-benzoyl chloride: To an oven-dried 100 mL round-bottom flask, 3-iodo-4-methyl-benzoic acid (0.79 g, 3 mmol) was stirred and refluxed under argon in thionyl chloride (4.55 mL, 62.28 mmol). Reaction was concentrated and brought up by 10 mL benzene. Solution was concentrated and placed under high vacuum, then dissolved in 3 mL THF resulting in a clear solution which was directly used in the next step.

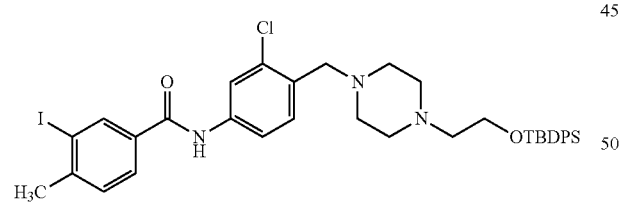

N-[4-[[4-[2-[tert-butyl(diphenyl)silyl]oxyethyl]piperazin-1-yl]methyl]-3-chloro-phenyl]-3-iodo-4-methyl-benzamide: 3-iodo-4-methylbenzoic acid (2.62 g, 10 mmol) was refluxed in SOCl₂ (10 mL) for 1 hr. The volatiles were removed, and the material was brought up in benzene (~10 mL). The solution was concentrated, and the material was placed on vacuum until solidification. The material was dissolved in 10 mL of THF. The resulting 3-iodo-4-methyl-benzoyl chloride (5.9 mL, 1M in THF) was added to a solution of 4-[[4-[2-[tert-butyl(diphenyl)silyl]oxyethyl]piperazin-1-yl]methyl]-3-chloro-aniline (5.89 mmol from previous step), DMAP (0.036 g, 0.29 mmol) and DIPEA (1.27 mL, 7.1 mmol) in THF (5.9 mL) under argon. The reaction was stirred at ambient temperature and followed by TLC. After ~18 hours, the reaction was quenched with MeOH (5 mL) and concentrated. The material was purified by flash column chromatography (0-10% MeOH in DCM) to afford the product as a white solid (3.40 g, 77% yield).

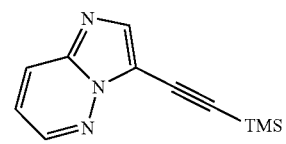 [SMILES: C[Si](C)(C)C#Cc1cnc2cccnn12]

2-imidazo[1,2-b]pyridazin-3-ylethynyl(trimethyl)silane: In a 50 mL round-bottom flask was combined 3-bromoimidazo[1,2-b]pyridazine (0.21 g, 1.07 mmol), a stir bar, copper (I) iodide (16.23 mg, 0.0900 mmol), and Pd(PPh₃)₄ (61.57 mg, 0.0500 mmol) under argon. The mixture was dissolved in anhydrous MeCN (1.5 mL) and then treated with trimethylsilylacetylene (0.3 mL, 2.13 mmol) and N,N-Diisopropylethylamine (0.28 mL, 1.6 mmol) before being sealed and heated to 80° C. overnight. The next morning, TLC (15% IPA in hexanes) showed complete conversion of the starting bromide to a less polar spot consistent with desired product, along with some slight contaminants. The product mixture was concentrated to a dark oil which was brought up in DCM and filtered over a plug of silica gel layered with Celite. The crude filtrate was used as-is in the next step.

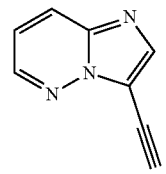

3-ethynylimidazo[1,2-b]pyridazine To a 20 mL microwave reaction vial were added 3-bromoimidazo[1,2-b]pyridazine (1.5 g, 7.58 mmol), PPh₃ (0.199 g, 0.76 mmol), Bis(acetonitrile)dichloropalladium (0.058 g, 0.38 mmol), CuI (0.072 g, 0.38 mmol), Et₃N (3.2 mL) and MeCN (7.5 mL). The reaction was sealed and sparged with argon for 30 min. To this solution was added TMS acetylene (3.15 mL, 22.7 mmol) and the reaction was irradiated to 80° C. overnight. The next day, the reaction was transferred to a flask, the volatiles were removed and the residue was brought up in methanol (7.5 mL). Potassium carbonate (2.1 g, 15.2 mmol) was added, and the mixture stirred for 1 hour. The solids were filtered over celite, and the filtrate was concentrated and purified by flash column chromatography (0-50% EtOAc in hexanes) to afford the product as a brown solid (0.80 g, 74% yield).

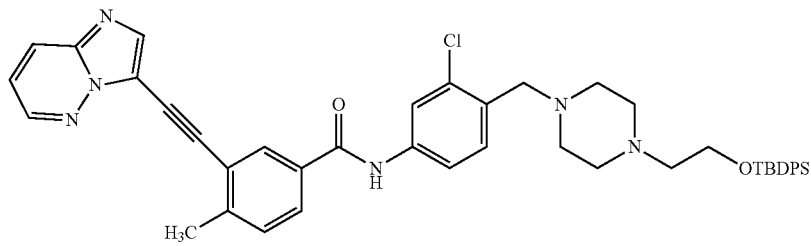

N-[4-[[4-[2-[tert-butyl(diphenyl)silyl]oxyethyl]piperazin-1-yl]methyl]-3-chloro-phenyl]-3-(2-imidazo[1,2-b]pyridazin-3-ylethynyl)-4-methyl-benzamide: 3-ethynylimidazo[1,2-b]pyridazine (0.4 g, 2.79 mmol), N-[4-[[4-[2-[tert-butyl(diphenyl)silyl]oxyethyl]piperazin-1-yl]methyl]-3-chloro-phenyl]-3-iodo-4-methyl-benzamide (1.62 g, 2.15 mmol), PPh$_3$ (0.147 g, 0.56 mmol), PdCl$_2$(CH$_3$CN)$_2$ (0.0362 g, 0.14 mmol) and CuI (0.039 g, 0.204 mmol) were combined in a flask and placed under argon. DIPEA (0.56 mL, 3.21 mmol) and DMF (16 mL) were added and the reaction was stirred overnight at ambient temperature. The reaction was quenched with 15 mL of water and extracted with EtOAc (3×75 mL). The organics were washed with brine (2×75 mL) and the organics were dried over Na$_2$SO$_4$. The organics were filtered and concentrated, and the material was purified by flash column chromatography (0-10% MeOH in DCM) to afford the product as a brown foam (1.54 g, 72% yield).

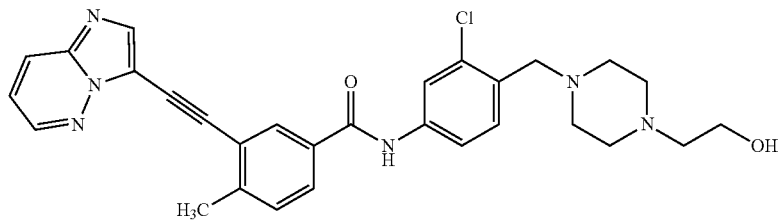 [SMILES: Cc1ccc(C(=O)Nc2ccc(CN3CCN(CCO)CC3)c(Cl)c2)cc1C#Cc1cnc2cccnn12]

N-[3-chloro-4-[[4-(2-hydroxyethyl)piperazin-1-yl]methyl]phenyl]-3-(2-imidazo[1,2-b]pyridazin-3-ylethynyl)-4-methyl-benzamide (TK3-141) To a stirred solution of N-[4-[[4-[2-[tert-butyl(diphenyl)silyl]oxyethyl]piperazin-1-yl]methyl]-3-chloro-phenyl]-3-(2-imidazo[1,2-b]pyridazin-3-ylethynyl)-4-methyl-benzamide (1.59 g, 2.07 mmol) in THF (17.6 mL) under argon was added TBAF (3.11 mL, 3.11 mmol, 1M in THF) and the reaction was followed by TLC. After ~1 hour, the reaction was concentrated and purified via two rounds of silica gel flash chromatography (0 to 20% MeOH in DCM) to yield the product as a light yellow solid (0.81 g, 73% yield); $^1$H NMR (400 MHz, CDCl$_3$) δ 8.60 (s, 1H), 8.47 (dd, J=4.4, 1.6 Hz, 1H), 8.08 (s, 1H), 8.02 (d, J=1.9 Hz, 1H), 7.92 (dd, J=9.2, 1.6 Hz, 1H), 7.81 (dd, J=9.1, 2.0 Hz, 2H), 7.56 (dd, J=8.4, 2.2 Hz, 1H), 7.42 (d, J=8.4 Hz, 1H), 7.34 (d, J=8.1 Hz, 1H), 7.11 (dd, J=9.2, 4.4 Hz, 1H), 3.63-3.59 (m, 4H), 3.48-3.47 (m, 4H), 2.59 (s, 3H), 2.55 (app t, J=5.6 Hz, 7H) ppm; $^{13}$C NMR (101 MHz, d$_6$-DMSO) δ 164.5, 145.1, 143.4, 139.7, 139.0, 138.3, 133.1, 132.3, 130.9, 130.6, 130.2, 130.1, 128.5, 126.1, 121.8, 120.4, 119.1, 118.7, 111.7, 96.4, 81.1, 60.3, 58.5, 58.3, 53.2, 52.7, 20.4 ppm; HRMS (APCI) m/z: [M+H]$^+$ Calcd for C$_{29}$H$_{30}$ClN$_6$O$_2$ 529.2113, Found 529.2107.

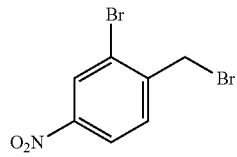 [SMILES: O=[N+]([O-])c1ccc(CBr)c(Br)c1]

2-bromo-1-(bromomethyl)-4-nitro-benzene: To a stirred, heated (80° C.) solution of 2-bromo-4-nitrotoluene (10.0 g, 46.3 mmol) and N-bromosuccinimide (8.24 g, 46.2 mmol) in anhydrous carbon tetrachloride (12 mL) was added, under Ar, benzoyl peroxide (224 mg, 0.69 mmol, 75% pure), and the resulting mixture was heated to reflux overnight. After cooling to room temperature, the mixture was diluted with Et$_2$O (100 mL), water was added (50 mL), and the phases were separated. The aqueous layer was extracted with Et$_2$O (2×100 mL), and the combined organic phases were dried with Na$_2$SO$_4$. After filtration and evaporation of the solvent, the residue was purified by column chromatography (0-40% EtOAc in Hexanes) to give pure 2-bromo-4-nitrobenzyl bromide as a yellow solid (8.5 g, 63% yield).

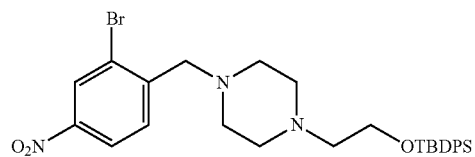

2-[4-[(2-bromo-4-nitro-phenyl)methyl]piperazin-1-yl]ethoxy-tert-butyl-diphenyl-silane To a solution of 2-bromo-5-nitro-bromomethyl benzene (2.4 g, 8.14 mmol) in CH$_2$Cl$_2$ (8.1 mL) was added Et$_3$N (1.13 mL, 8.14 mmol) and tert-butyl-diphenyl-(2-piperazin-1-ylethoxy)silane (3 g, 8.14 mmol) under argon, and the reaction stirred at ambient temperature with monitoring by TLC. After ~24 hours, a saturated aqueous solution of NaHCO$_3$ was added (10 mL) and diluted with 15 mL of water, and the mixture was extracted with CH$_2$Cl$_2$ (3×75 mL). The combined organic layer was dried over Na$_2$SO$_4$, filtered, concentrated, and the resulting residue was purified by silica gel chromatography (0-20% EtOAc in hexanes) to provide the product as an orange oil (3.35 g, 71% yield).

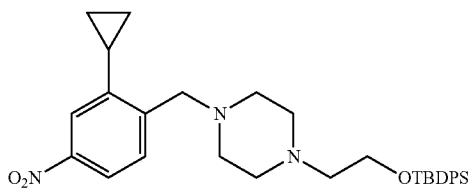

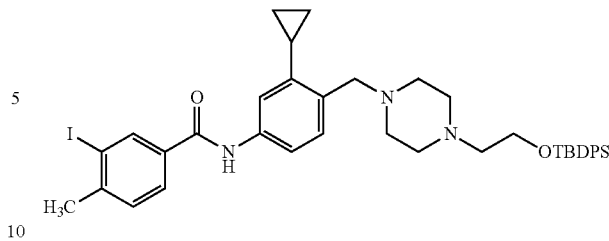

tert-butyl-[2-[4-[(2-cyclopropyl-4-nitro-phenyl)methyl] piperazin-1-yl]ethoxy]-diphenyl-silane: A solution of 2-[4-[(2-bromo-4-nitro-phenyl)methyl]piperazin-1-yl]ethoxy-tert-butyl-diphenyl-silane (1.75 g, 3.0 mmol), cyclopropylboronic acid (0.773 g, 9.0 mmol), $K_3PO_4$ (2.87 g, 13.5 mmol), Pd(OAc)$_2$ (67 mg, 0.3 mmol), and tricyclohexylphosphine (0.168 g, 0.6 mmol) in toluene (15 mL) and water (3 mL) was degassed with argon and then heated to 100° C. via microwave irradiation for ~6 hours. The reaction was quenched with 25 mL of saturated aqueous $NaHCO_3$ solution and extracted with DCM (3×75 mL). The organics were dried over $Na_2SO_4$, filtered and concentrated. The material was purified via flash column chromatography (0-30% MeOH in DCM) to yield the product as an orange solid (1.55 g, 95% yield).

N-[4-[[4-[2-[tert-butyl(diphenyl)silyl]oxyethyl]piperazin-1-yl]methyl]-3-cyclopropyl-phenyl]-3-iodo-4-methyl-benzamide 3-iodo-4-methylbenozic acid (2.62 g, 10 mmol) was refluxed in $SOCl_2$ (10 mL) for 1 hr. The volatiles were removed, and the material was brought up in benzene (~10 mL). The solution was concentrated, and the material was placed on vacuum until solidification. The material was dissolved in 10 mL of THF. The resulting 3-iodo-4-methyl-benzoyl chloride (1.8 mL, 1M in THF) was added to a solution of 4-[[4-[2-[tert-butyl(diphenyl)silyl]oxyethyl]piperazin-1-yl]methyl]-3-cyclopropyl-aniline (0.93 g, 1.81 mmol), DMAP (0.011 g, 0.091 mmol) and DIPEA (0.39 mL, 2.17 mmol) in THF (1.8 mL) under argon. The reaction stirred at ambient temperature overnight and was followed by TLC. The reaction was quenched with MeOH (5 mL) and concentrated. The material was purified by flash column chromatography (0-10% MeOH in DCM) to afford the product as a white solid (0.96 g, 70% yield).

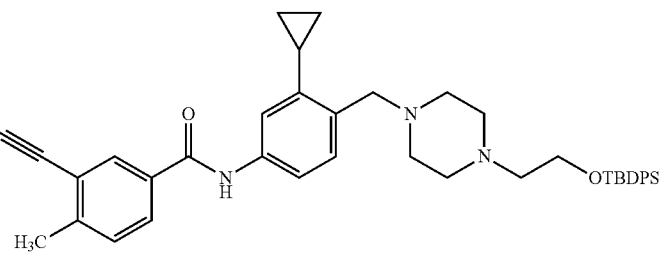

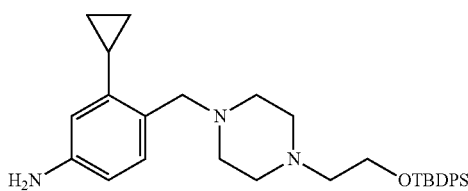

4-[[4-[2-[tert-butyl(diphenyl)silyl]oxyethyl]piperazin-1-yl]methyl]-3-cyclopropyl-aniline: A solution of tert-butyl-[2-[4-[(2-cyclopropyl-4-nitro-phenyl)methyl]piperazin-1-yl]ethoxy]-diphenyl-silane (1.55 g, 2.85 mmol) in ethyl acetate (61 ml) was catalytically hydrogenated over 5% platinum on carbon (489 mg, 0.1254 mmol) under a balloon of $H_2$ gas at ambient temperature overnight. The reaction mixture was filtered through celite, and the filtrate was concentrated to give the desired material as a green residue (0.93 g, 63% yield).

N-[4-[[4-[2-[tert-butyl(diphenyl)silyl]oxyethyl]piperazin-1-yl]methyl]-3-cyclopropyl-phenyl]-3-(2-imidazo[1,2-b]pyridazin-3-ylethynyl)-4-methyl-benzamide: N-[4-[[4-[2-[tert-butyl(diphenyl)silyl]oxyethyl]piperazin-1-yl]methyl]-3-cyclopropyl-phenyl]-3-iodo-4-methyl-benzamide (0.76 g, 1.01 mmol), 3-ethynylimidazo[1,2-b]pyridazine (0.188 g, 1.32 mmol) $PdCl_2(CH_3CN)_2$ (17 mg, 0.066 mmol), CuI (0.018 mg, 0.096 mmol) and $PPh_3$ (69 mg, 0.262 mmol) were combined in a flask under argon. DMF (7.6 mL) and DIPEA (0.26 mL) were added. The reaction was stirred at ambient temperature overnight and followed by TLC. The reaction was quenched by the addition of 50 mL of brine and extracted with DCM (3×100 mL). The organics were dried over $Na_2SO_4$, filtered and concentrated. The material was purified by flash column chromatography (0-15% MeOH in DCM) to afford the product as a beige solid (0.256 g, 33% yield).

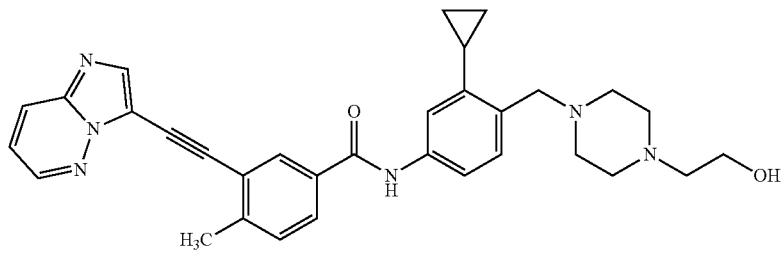 [SMILES: Cc1ccc(C(=O)Nc2ccc(CN3CCN(CCO)CC3)c(C3CC3)c2)cc1C#Cc1cnc2cccnn12]

N-[3-cyclopropyl-4-[[4-(2-hydroxyethyl)piperazin-1-yl]methyl]phenyl]-3-(2-imidazo[1,2-b]pyridazin-3-ylethynyl)-4-methyl-benzamide (TK3-144): N-[4-[[4-[2-[tert-butyl(diphenyl)silyl]oxyethyl]piperazin-1-yl]methyl]-3-cyclopropyl-phenyl]-3-(2-imidazo[1,2-b]pyridazin-3-ylethynyl)-4-methyl-benzamide (251 mg, 0.325 mmol) was dissolved in THF (2.8 mL) under Ar and TBAF (0.33 mL, 0.33 mmol, 1 M in THF) was added. The reaction was stirred at ambient temperature overnight. The next day, the reaction was concentrated and purified by silica gel flash chromatography (0-15% MeOH in DCM) to afford the title compound (157 mg, 91% yield); $^1$H NMR (400 MHz, $d_6$-DMSO) δ 10.20 (s, 1H), 8.74 (s, 1H), 8.31-8.22 (m, 2H), 8.19 (s, 1H), 7.93 (d, J=7.6 Hz, 1H), 7.64 (d, J=8.1 Hz, 1H), 7.53 (d, J=7.9 Hz, 1H), 7.43-7.37 (m, 1H), 7.34 (s, 1H), 7.20 (d, J=7.6 Hz, 1H), 4.40 (s, 1H), 3.55 (s, 2H), 3.48 (s, 2H), 3.36 (s, 4H), 2.60 (s, 3H), 2.51 (s, 2H), 2.47-2.34 (m, 6H), 2.24-2.17 (m, 1H), 0.94 (d, J=6.7 Hz, 2H), 0.60 (s, 2H) ppm; $^{13}$C NMR (101 MHz, $d_6$-DMSO) δ 164.1, 145.1, 143.1, 142.3, 138.2, 138.1, 132.7, 132.6, 130.1, 130.0, 129.7, 128.4, 126.1, 121.7, 119.1, 117.1, 116.8, 111.7, 109.6, 96.5, 81.0, 60.3, 59.4, 58.5, 53.3, 52.8, 20.4, 12.3, 7.6 ppm; HRMS (APCI) m/z: [M−H]$^-$ Calcd for $C_{32}H_{33}N_6O_2$ 533.2670; Found 533.2679.

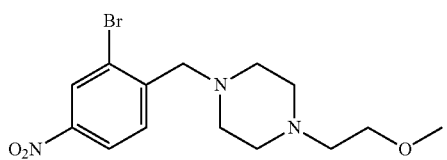 [SMILES: COCCN1CCN(Cc2ccc([N+](=O)[O-])cc2Br)CC1]

1-[(2-bromo-4-nitro-phenyl)methyl]-4-(2-methoxyethyl)piperazine To a solution of 2-bromo-5-nitro-bromomethyl benzene (2.4 g, 8.14 mmol) in $CH_2Cl_2$ (8.1 mL) was added $Et_3N$ (1.13 mL, 8.14 mmol) and 1-(2-methoxyethyl)piperazine (1.1735 g, 8.14 mmol) under argon. The reaction stirred at ambient temperature with monitoring by TLC. After ~24 hours, the reaction was quenched with saturated aqueous $NaHCO_3$ solution (10 mL) and diluted with 15 mL of water, and the mixture was extracted with $CH_2Cl_2$ (3×75 mL). The combined organic layer was dried over $Na_2SO_4$, filtered, concentrated, and the resulting residue was purified by silica gel chromatography (0-30% MeOH in DCM with 1% triethylamine) to afford the desired product as a yellow oil (2.19 g, 75% yield).

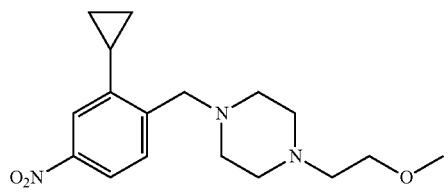 [SMILES: COCCN1CCN(Cc2ccc(N)cc2C2CC2)CC1]

1-[(2-cyclopropyl-4-nitro-phenyl)methyl]-4-(2-methoxyethyl)piperazine In 20-mL a microwave vial, a yellow solution of 1-[(2-bromo-4-nitro-phenyl)methyl]-4-(2-methoxyethyl)piperazine (1.07 g, 3 mmol), cyclopropylboronic acid (0.77 g, 9 mmol), potassium phosphate (tribasic) (2.87 g, 13.5 mmol), palladium(II) acetate (0.07 g, 0.30 mmol), and tricyclohexylphosphine (0.17 g, 0.60 mmol) in toluene (15 mL) and water (3 mL) was degassed with argon for ~30 minutes before being heated at 100° C. overnight for 12 hours via microwave irradiation whereupon the reaction changed to a dark black-green color. The reaction was diluted with ethyl acetate and quenched with saturated sodium bicarbonate solution before the product was extracted with ethyl acetate (2×40 mL) then DCM (1×40 mL). The organic extracts were combined and dried over sodium sulfate before the solids were filtered over a pad of celite; the yellow filtrate was concentrated to ~1.4 g of yellow oil which was purified via silica gel flash column chromatography (0-15% methanol in DCM) to afford the desired product (0.992 g, >99% yield). HRMS (ESI) m/z: [M+H]$^+$ Calcd for $C_{17}H_{26}N_3O_3$ 320.19687; found 320.19648.

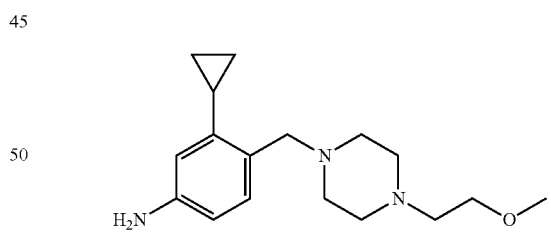

3-cyclopropyl-4-[[4-(2-methoxyethyl)piperazin-1-yl]methyl]aniline In a 200-mL round-bottom flask was 1-[(2-cyclopropyl-4-nitro-phenyl)methyl]-4-(2-methoxyethyl)piperazine (6.0 mL, 2.06 mmol). A stir bar and 3-way glass adapter were added, and the material was dried briefly before the flask was charged with argon, platinum on carbon (0.32 g, 0.08 mmol), and ethyl acetate (30 mL) to give a black suspension. The atmosphere was evacuated and restored with hydrogen gas, and the reaction stirred at ambient temperature overnight. The next day, the reaction mixture was filtered through celite, and the filtrate was concentrated to give the desired material as a yellow oil (0.57 g, 96% yield).

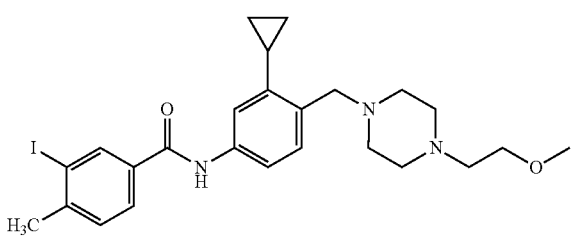 [SMILES: COCCN1CCN(Cc2ccc(NC(=O)c3ccc(C)c(I)c3)cc2C2CC2)CC1]

N-[3-cyclopropyl-4-[[4-(2-methoxyethyl)piperazin-1-yl]methyl]phenyl]-3-iodo-4-methyl-benzamide: 3-iodo-4-methyl-benzoic acid (1.05 g, 4 mmol) was refluxed in thionyl chloride (6.1 mL, 84 mmol) for ~1 hour. The reaction was concentrated on a rotovap, and the material was brought up in benzene (~10 mL). The solution was concentrated, and the material was placed on vacuum until solidification. The material was dissolved in 4 mL of anhydrous THE to make a ~1 M solution be used directly. Under an argon atmosphere, the freshly prepared 3-iodo-4-methyl-benzoyl chloride (3.1 mL, 3.1 mmol) was added to a solution of 3-cyclopropyl-4-[[4-(2-methoxyethyl)piperazin-1-yl]methyl]aniline (0.9 g, 3.1 mmol), DMAP (0.02 g, 0.15 mmol)) and N,N-diisopropylethylamine (0.67 mL, 3.72 mmol) in anhydrous THE (3.1 mL). The reaction was stirred at ambient temperature overnight; TLC (90:10 EtOAc:MeOH) the next morning showed complete conversion to a less polar product. The reaction was quenched with MeOH (5 mL) and concentrated before being purified via two rounds of silica gel flash column chromatography (0-20% methanol in DCM) to afford the desired product (1.4 g, 85% yield); HRMS (APCI) m/z: [M+H]+ calcd for $C_{25}H_{33}IN_3O_2$ 534.1612, found 534.1616.

again washed with saturated aqueous ammonium chloride. The organic was dried, filtered and concentrated to afford the product as a thin orange film (84 mg, 31% yield); $^1$H NMR (600 MHz, CDCl$_3$) δ 8.49-8.46 (m, 1H), 8.21 (s, 1H), 8.07 (s, 1H), 8.04 (d, J=1.7 Hz, 1H), 7.96 (d, J=9.0 Hz, 1H), 7.82 (dd, J=7.9, 1.8 Hz, 1H), 7.47 (dd, J=8.1, 1.9 Hz, 1H), 7.36 (d, J=8.0 Hz, 1H), 7.34 (s, 1H), 7.12 (dd, J=9.1, 4.3 Hz, 1H), 3.77 (s, 2H), 3.70 (s, 2H), 3.34 (s, 3H), 2.95-2.74 (m, 10H), 2.61 (s, 3H), 2.15-2.07 (m, 1H), 0.94 (d, J=8.2 Hz, 2H), 0.67 (d, J=4.3 Hz, 2H) ppm; $^{13}$C NMR (151 MHz, CDCl$_3$) □ 165.0, 144.4, 144.3, 144.1, 143.6, 139.9, 138.5, 132.7, 130.8, 130.3, 130.2, 128.0, 126.2, 126.1, 122.9, 117.9, 117.8, 117.7, 113.2, 96.9, 80.8, 68.7, 59.0, 57.4, 53.1, 51.1, 29.8, 21.1, 13.0, 7.8 ppm; HRMS (APCI) m/z: [M+H]+ Calcd for $C_{33}H_{37}N_6O_2$, 549.2973; Found 549.2992.

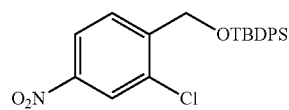

tert-butyl-[(2-chloro-4-nitro-phenyl)methoxy]-diphenyl-silane In an oven-dried 250-mL round bottom flask with stir bar was dissolved (2-chloro-4-nitro-phenyl)methanol (8.69 g, 46.35 mmol) in anhydrous DMF (16 mL) to give a light yellow solution. IMIDAZOLE (6.31 g, 92.69 mmol) was added, and the mixture was cooled to 0° C. before tert-butyldiphenylchlorosilane (14.29 mL, 55.61 mmol) was added dropwise. The reaction was heated to 50° C. and followed by TLC. After ~2 hours, the reaction was cooled to 0° C. and quenched by addition of 35 mL of 1 M NaOH dropwise, whereupon the reaction bubbled vigorously and

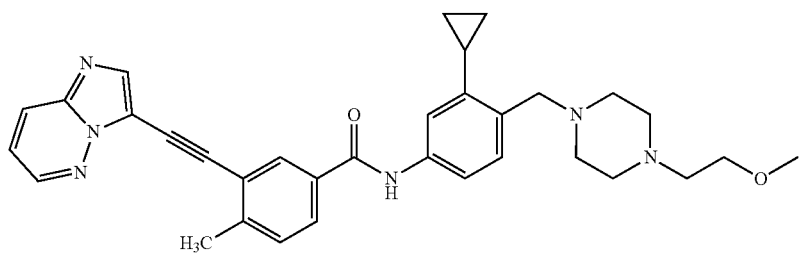 [SMILES: COCCN1CCN(Cc2ccc(NC(=O)c3ccc(C)c(C#Cc4cnc5cccnn45)c3)cc2C2CC2)CC1]

N-[3-cyclopropyl-4-[[4-(2-methoxyethyl)piperazin-1-yl]methyl]phenyl]-3-(2-imidazo[1,2-b]pyridazin-3-ylethynyl)-4-methyl-benzamide (CD-1-002) 3-ethynylimidazo[1,2-b]pyridazine (70 mg, 0.49 mmol), N-[3-cyclopropyl-4-[[4-(2-methoxyethyl)piperazin-1-yl]methyl]phenyl]-3-iodo-4-methyl-benzamide (200 mg, 0.37 mmol), triphenylphosphine (26 mg, 0.1 mmol), dichlorobis(acetonitrile)palladium(II) (6.32 mg, 0.02 mmol), and copper(I) iodide (6.96 mg, 0.0400 mmol) were combined in a flask and the atmosphere was cycled 3× with argon. (N-ethyldiisopropylamine) (0.13 mL, 0.56 mmol) and DMF (1.5 mL) were added and the reaction was stirred at room temperature overnight. The next day, TLC showed the reaction was complete, so it was quenched with 15 mL DI water and washed with 2×75 mL ethyl acetate. Organic layers were combined and washed with 2×75 mL brine solution. Organics were dried over Na$_2$SO$_4$ and concentrated. The residue was purified via two rounds of silica gel flash chromatography (0 to 20% MeOH/DCM). and the compound was changed to a deep yellow color with complete dissolution of the white solid. After stirring for ~10 minutes, the THF was evaporated and the product was extracted with ethyl acetate (~150 mL) and brine (~150 mL). The organic extract was dried over sodium sulfate, filtered and concentrated to yield tert-butyl-[(2-chloro-4-nitro-phenyl)methoxy]-diphenyl-silane as an orange solid (22.6 g, 53.1 mmol, >99% yield).

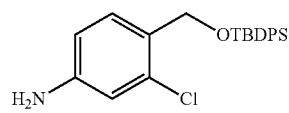

4-[[tert-butyl(diphenyl)silyl]oxymethyl]-3-chloro-aniline A solution of tert-butyl-[(2-chloro-4-nitro-phenyl)methoxy]-diphenyl-silane (10.23 g, 24.02 mmol) in ethyl acetate (150 mL) was catalytically hydrogenated over Pt (4.12 g, 1.06 mmol) under H$_2$ gas. Reaction was left overnight at ambient temperature. The next day, the reaction was filtered over celite and concentrated to yield 4-[[tert-butyl(diphenyl)silyl]oxymethyl]-3-chloro-aniline as an orange oil (9.62 g, 24.3 mmol, >99% yield).

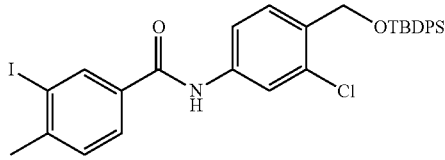

N-[4-[[tert-butyl(diphenyl)silyl]oxymethyl]-3-chloro-phenyl]-3-iodo-4-methyl-benzamide To an oven-dried 100 mL flask with stirrer, 3-iodo-4-methyl-benzoyl chloride (1.71 mL, 1.71 mmol) was added to a solution of 4-[[tert-butyl(diphenyl)silyl]oxymethyl]-3-chloro-aniline (0.68 g, 1.71 mmol), N,N-Diisopropylethylamine (0.36 mL, 2.06 mmol), and 4-dimethylaminopyridine (10.47 mg, 0.0900 mmol) in anhydrous THE (8 mL). Reaction was stirred under argon overnight. The next day, the reaction was quenched with 2 mL methanol. The product mixture was adsorbed onto celite and purified via silica gel flash column chromatography (0 to 20% EtoAc/Hex) to yield N-[4-[[tert-butyl(diphenyl)silyl]oxymethyl]-3-chloro-phenyl]-3-iodo-4-methyl-benzamide as a white foam (946.7 mg, 1.48 mmol, 86.3% yield).

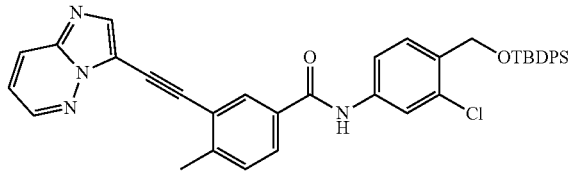

N-[4-[[tert-butyl(diphenyl)silyl]oxymethyl]-3-chloro-phenyl]-3-(2-imidazo[1,2-b]pyridazin-3-ylethynyl)-4-methyl-benzamide: In a 2-neck round-bottom flask with stir bar were combined N-[4-[[tert-butyl(diphenyl)silyl]oxymethyl]-3-chloro-phenyl]-3-iodo-4-methyl-benzamide (2 g, 3.12 mmol), 3-ethynylimidazo[1,2-b]pyridazine (0.6 g, 4.22 mmol) triphenylphosphine (204.9 mg, 0.7800 mmol), copper(I) iodide (59.51 mg, 0.3100 mmol), and dichlorobis(acetonitrile)palladium(II) (52.69 mg, 0.2000 mmol) under argon. The solids were dissolved in anhydrous DMF (10 mL) before N,N-diisopropylethylamine (0.82 mL, 4.69 mmol) was added with stirring, and the reaction stirred under argon at ambient temperature overnight. The next morning, TLC (1:1 DCM:EtOAC) showed conversion of the UV-active iodide and fluorescent alkyne starting materials to a new fluorescent spot of intermediate polarity. Hence, the reaction was diluted with ethyl acetate and quenched with water before the product was extracted with ethyl acetate and twice washed with brine solution. The organic layer was dried over sodium sulfate, filtered and concentrated to a yellow oil. The sample was adsorbed onto silica gel purified via flash chromatography (0-50% gradient of ethyl acetate in DCM). All fractions containing the desired spot were concentrated to afford the desired compound as a white solid (1.7 g, 83% yield).

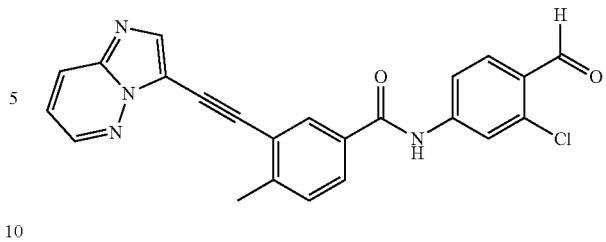

In a 250-mL round-bottom flask with stir bar was dissolved N-[4-[[tert-butyl(diphenyl)silyl]oxymethyl]-3-chloro-phenyl]-3-(2-imidazo[1,2-b]pyridazin-3-ylethynyl)-4-methyl-benzamide (3.03 g, 4.62 mmol) in anhydrous THF (19 mL) to give a dark orange solution. Then tetra-n-butylammonium fluoride trihydrate (1.6 g, 5.08 mmol) was added as a freshly dissolved solution in THE (5 mL). The reaction was capped and stirred at ambient temperature overnight. The next day, TLC (90:10 DCM:MeOH) showed spot-to-spot conversion to a more polar product. Addition of methanol to the reaction precipitated a solid; the volatiles were removed and the solid was triturated with hexanes and collected (1.45 g, 75% yield);

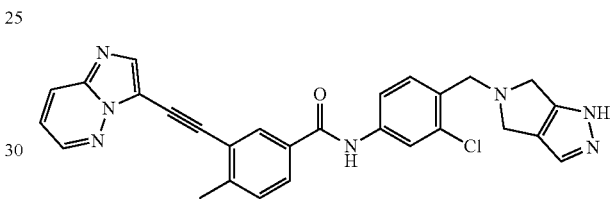

N-[3-chloro-4-(4,6-dihydro-1H-pyrrolo[3,4-c]pyrazol-5-ylmethyl)phenyl]-3-(2-imidazo[1,2-b]pyridazin-3-ylethynyl)-4-methyl-benzamide (ZD-3-167): To an oven-dried 25-mL Schlenk tube with stir bar was added powdered 4 Å molecular sieves which were then flame-activated under vacuum. After the apparatus was allowed to cool, N-(3-chloro-4-formyl-phenyl)-3-(2-imidazo[1,2-b]pyridazin-3-ylethynyl)-4-methyl-benzamide (200 mg, 0.48 mmol) and 1,4,5,6-tetrahydropyrrolo[3,4-c]pyrazole (63 mg, 0.58 mmol) were added under argon and dissolved in anhydrous DMSO (1.5 mL) to give a light yellow mixture. The reaction was heated to 50° C. for ~2 hours after which time acetic acid (15 uL, 0.27 mmol) was added and the reaction was left to stir another ~1.5 hours. The reaction was allowed to cool to ambient temperature before sodium triacetoxyborohydride (307 mg, 1.45 mmol) was added in one portion; the reaction was brought back up to temperature and stirred for ~30 minutes when TLC showed the reaction was complete. The reaction was allowed to cool to ambient temperature before being carefully added to a saturated sodium bicarbonate solution in a separatory funnel to quench. The heterogeneous product mixture was twice extracted with ethyl acetate, and the organic was washed with water and brine (4×), being sure to collect residual insoluble solids, before being dried over sodium sulfate, filtered and concentrated. The product was adsorbed onto Celite to dry load a 12 g RediSep CombiFlash silica gel column for purification and was eluted with 100% diethyl ether for 1 minute, followed by a gradient of 0-15% methanol in diethyl ether over 15 minutes. The diethyl ether was substituted with DCM, and the product was eluted with 15% methanol in DCM (isocratic). The appropriate fractions were concentrated to afford the product as a yellow solid (80 mg, 33% yield); $^1$H NMR (300 MHz, DMSO-$d_6$) δ 12.40 (br s, 1H), 10.46 (s, 1H), 8.73 (dd, J=4.5, 1.6 Hz, 1H), 8.23 (m, 3H), 8.01 (d, J=2.0 Hz, 1H), 7.94 (dd, J=8.0, 1.9 Hz, 1H), 7.75 (dd, J=8.3, 2.1 Hz, 1H), 7.54 (dd, J=8.4, 3.3 Hz, 2H), 7.39 (m, 2H), 3.99 (s, 2H), 3.72 (s, 4H), 2.61 (s, 3H) ppm; $^{13}$C NMR (101 MHz, DMSO-d$_6$) δ 164.5, 156.5, 145.1, 143.4, 139.7, 139.1, 138.3, 132.7, 132.4, 131.6, 130.7, 130.2, 130.1, 128.5, 126.1, 121.8, 120.8, 120.5, 120.0, 119.1, 118.8, 111.7, 96.5, 81.2, 56.1, 51.1, 50.9, 20.4 ppm; HRMS (APCI) m/z: [M−H]⁻ Calcd for C$_{21}$H$_{21}$ClN$_7$O 506.15016, found 506.15061.

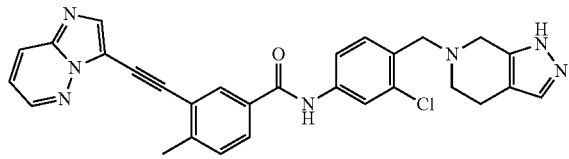 [SMILES: Cc1ccc(C(=O)Nc2ccc(CN3CCc4cn[nH]c4C3)c(Cl)c2)cc1C#Cc1cnc2cccnn12]

N-[3-chloro-4-(1,4,5,7-tetrahydropyrazolo[3,4-c]pyridin-6-ylmethyl)phenyl]-3-(2-imidazo[1,2-b]pyridazin-3-ylethynyl)-4-methyl-benzamide (CD-1-051): In an oven-dried 4-mL vial with stirrer under argon, 4,5,6,7-tetrahydro-1H-pyrazolo[3,4-c]pyridine (27 mg, 0.22 mmol) was dissolved in DMSO (0.5 mL) and acetic acid (0.05 mL). N-(3-chloro-4-formyl-phenyl)-3-(2-imidazo[1,2-b]pyridazin-3-ylethynyl)-4-methyl-benzamide (55 mg, 0.13 mmol) and sodium triacetoxyborohydride (84 mg, 0.4 mmol) were added and the mixture was stirred at 50° C. and followed by TLC. After two hours, the reaction was quenched with sodium bicarbonate, extracted with ethyl acetate, and washed with brine solution. Organics were combined with a previous replicate of this experiment and dry loaded with Celite onto a 24 g RediSep CombiFlash silica gel column for purification (0-10% MeOH/DCM). Fractions of interest were combined and concentrated via rotary evaporation to afford a beige solid; $^1$H NMR (400 MHz, CDCl$_3$) δ 9.06 (s, 1H), 8.42 (dd, J=4.4, 1.6 Hz, 1H), 8.03 (s, 1H), 7.99 (d, J=1.7 Hz, 1H), 7.88 (dd, J=9.3, 1.5 Hz, 1H), 7.83 (d, J=2.0 Hz, 1H), 7.76 (dd, J=8.0, 1.8 Hz, 1H), 7.50 (dd, J=8.4, 2.0 Hz, 1H), 7.42 (d, J=8.42 Hz, 1H), 7.24 (s, 1H), 7.07 (dd, J=9.2, 4.4 Hz, 1H), 3.77 (s, 2H), 3.62 (s, 2H), 2.78 (t, J=5.3 Hz, 2.64 (t, J=5.11, 2H), 2.53 (s, 3H) ppm; $^{13}$C NMR (101 MHz, DMSO-d$_6$) δ 167.0, 149.8, 146.3, 143.3, 137.6, 137.1, 135.2, 133.3, 132.4, 131.3, 130.3, 127.6, 127.4, 123.3, 122.4, 122.3, 120.6, 116.0, 99.4, 79.5, 78.0, 57.1, 51.8, 21.0, 18.8 ppm [$^1$H NMR was taken on the indicated amine, while $^{13}$C NMR was taken on the HCl salt]; HRMS (NSI) m/z [M+H]⁺ Calcd for C$_{29}$H$_{25}$ClN$_7$O [M+H]⁺, 522.18036; found, 522.18104.

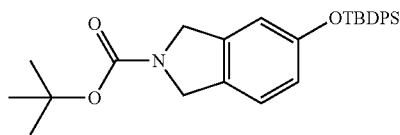

tert-butyl 5-[tert-butyl(diphenyl)silyl]oxyisoindoline-2-carboxylate (CD-1-054). In an oven-dried 250 mL round bottom flask with stirrer under argon, tert-butyl 5-hydroxyisoindoline-2-carboxylate (825 mg, 3.51 mmol) was dissolved in DMF (3.3 mL) to give a light brown solution. Tert-butyldiphenylchlorosilane (1.08 mL, 4.21 mmol) was added, immediately darkening the solution. Imidazole (597 mg, 8.77 mmol) was then added, lightening the solution color back to light brown. The reaction stirred for 30 minutes, after which time the mixture was diluted with water, extracted with ethyl acetate, and washed with brine 3 times. The organic layer was dried over Na$_2$SO$_4$, filtered, and concentrated, yielding an orange solid. The solid was purified using flash chromatography (0-50% EtOAc/Hex). Fractions of interest were combined to yield tert-butyl 5-[tert-butyl(diphenyl)silyl]oxyisoindoline-2-carboxylate as a white solid (1080 mg, 65.0% yield); $^1$H NMR (400 MHz, CDCl$_3$) δ 7.72 (m, 4H), 7.40 (m, 6H), 6.93 (dd, J=33.9, 8.3 Hz, 1H), 6.65 (m, 2H), 4.52 (d, J=20.6 Hz, 2H), 4.47 (d, J=24.4 Hz, 2H), 1.49 (d, J=4.3 Hz, 9H), 1.10 (m, 9H) ppm; $^{13}$C NMR (125 MHz, CDCl$_3$) δ 155.3, 154.6 (d, J=5 Hz), 138.5, 138.3, 135.6, 135.4, 135.0, 132.9, 130.1, 129.7, 129.4, 127.9, 127.8, 123.4, 123.0, 119.2, 119.1, 114.1, 113.7, 79.7, 52.0 (dd, J=66, 39 Hz, 2C), 28.7, 26.7, 26.6 ppm; HRMS (NSI+) m/z: [M+H]⁺ calcd for C$_{29}$H$_{36}$NO$_3$Si 474.24590, found 474.24636.

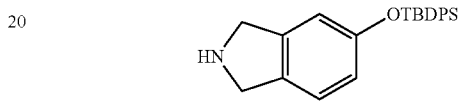

tert-butyl-isoindolin-5-yloxy-diphenyl-silane (ZD-3-172). In a flame-dried 50-mL round-bottom flask with stir bar was dissolved tert-butyl 5-[tert-butyl(diphenyl)silyl]oxyisoindoline-2-carboxylate (0.67 g, 1.41 mmol) in anhydrous DCM (6 mL) to give a colorless solution. The solution was chilled to 0° C. with an ice bath before being dropwise treated with trifluoroacetic acid (0.66 mL, 8.57 mmol); after ~2 hours, another half portion of trifluoroacetic acid (0.33 mL, 4.31 mmol) (for a total of 9 eq, 0.99 mL, 12.88 mmol) was added, and the reaction was allowed to stir an additional hour. The reaction was quenched by dropwise addition of a slight excess of triethylamine (2.4 mL, 13.78 mmol). The reaction mixture was adsorbed onto silica gel and purified via flash chromatography, eluting with 100% DCM for 2 minutes followed by a gradient of 0-10% methanol over 15 minutes. Fractions of interest were concentrated to yield a pink oil and then brought up in a mixture of ethyl acetate and diethyl ether and washed with water and brine before being dried over sodium sulfate, filtered and concentrated to a dark oil (0.415 g, 76% yield); $^1$H NMR (600 MHz, CDCl$_3$) δ 10.31 (s, 1H), 7.66 (m, 4H), 7.37 (m, 6H), 6.92 (d, J=8.4 Hz, 1H), 6.66 (m, 2H), 4.43 (dt, J=27.6, 5.2 Hz, 4H), 1.07 (s, 9H); $^{13}$C NMR (100 MHz, CDCl$_3$) δ 196.3, 156.5, 135.5, 135.2, 132.3, 130.3, 128.1, 126.0, 123.5, 120.7, 114.0, 50.4, 50.2, 26.5 (3C), 19.5 ppm; HRMS (NSI+) m/z: [M+H]⁺ calcd for C$_{24}$H$_{28}$NOSi 374.19347, found 374.19399.

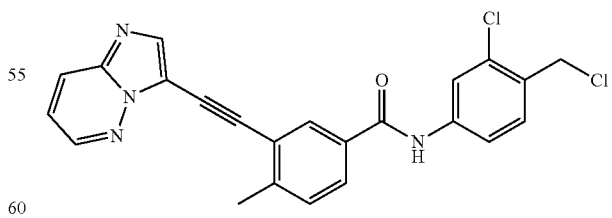

N-(3-chloro-4-(chloromethyl)phenyl)-3-(imidazo[1,2-b]pyridazin-3-ylethynyl)-4-methylbenzamide (ZD-3-174) In an oven-dried 25-mL Schlenk tube with stir bar was suspended N-[3-chloro-4-(hydroxymethyl)phenyl]-3-(2-imidazo[1,2-b]pyridazin-3-ylethynyl)-4-methyl-benzamide (90 mg, 0.22 mmol) in anhydrous THF (1 mL) to give a beige suspension; an equivolume amount of anhydrous NMP (1 mL) was added as co-solvent, somewhat solubilizing the mixture. To this mixture was added triethylamine (0.2 mL, 1.44 mmol) followed by dropwise addition of thionyl chloride (0.1 mL, 1.37 mmol), which released a vapor. The reaction stirred at ambient temperature for ~2 hours with monitoring by TLC (95:5 DCM:MeOH). The reaction was chilled with an ice bath before being diluted with ethyl acetate and quenched with water. The product mixture was extracted with ethyl acetate and neutralized with saturated sodium bicarbonate solution before being washed with brine solution and 0.1 N HCl solution to remove residual TEA. The organic was dried over sodium sulfate, filtered and concentrated to a crude brown solid which was purified via silica gel flash chromatography. The product was eluted with 100% DCM for 2 minutes followed by a 0-10% gradient of methanol in DCM over 10 minutes. The fractions of interest were pooled and concentrated to afford the desired product (69 mg, 73% yield); $^1$H NMR (400 MHz, CD$_3$OD) δ 8.56 (dd, J=4.4, 1.6 Hz, 1H), 8.14 (d, J=2.0 Hz, 1H), 8.03 (dd, J=9.2, 1.6 Hz, 1H), 8.00 (s, 1H), 7.93, (d, J=2.2 Hz, 1H), 7.84 (dd, J=8.0, 2.0 Hz, 1H), 7.62 (dd, J=8.4, 2.2 Hz, 1H), 7.43 (d, J=8.4 Hz, 1H), 7.40 (d, J=8.1 Hz, 1H), 7.28 (dd, J=9.2, 4.5 Hz, 1H), 4.69 (s, 2H), 2.63 (s, 3H) ppm; HRMS (APCI+) m/z: [M+H]$^+$ calcd for C$_{23}$H$_{17}$Cl$_2$N$_4$O 435.07739, found 435.07780.

Hz, 1H), 6.58 (dd, J=8.1, 2.4 Hz, 1H), 3.96 (s, 2H), 3.88 (s, 2H), 3.84 (s, 2H), 2.65 (s, 3H), 1.08 (s, 9H) ppm; $^{13}$C NMR (100 MHz, CDCl$_3$) δ 164.7, 154.6, 144.5, 143.9, 141.2, 139.7, 138.4, 137.6, 135.5, 134.2, 132.9, 132.7, 132.3, 132.2, 130.9, 130.2, 130.0, 129.8, 127.8, 127.7, 125.9, 122.8, 122.6, 120.9, 118.4, 118.0, 117.8, 113.7, 113.0, 96.6, 80.8, 59.1, 58.5, 56.3, 26.5 (3C), 20.9, 19.4 ppm; HRMS (APCI-) m/z: [M−H]$^−$ calcd for C$_{47}$H$_{41}$ClN$_5$O$_2$Si 770.27235, found 770.27372.

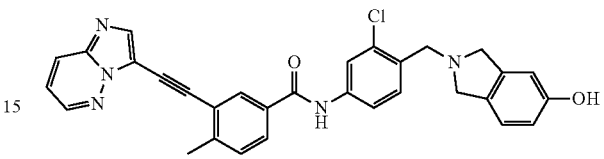

N-(3-chloro-4-((5-hydroxyisoindolin-2-yl)methyl)phenyl)-3-(imidazo [1,2-b]pyridazin-3-ylethynyl)-4-methyl-benzamide (CD-1-066) To a 5-dram vial under Ar was added N-[4-[[5-[tert-butyl(diphenyl)silyl]oxyisoindolin-2-yl]methyl]-3-chloro-phenyl]-3-(2-imidazo[1,2-b]pyridazin-3-ylethynyl)-4-methyl-benzamide (100 mg, 0.13 mmol). TBAF (0.4 mL, 0.4 mmol) was added as a ~1 M solution in THF, and the reaction stirred overnight. After 24 hours,

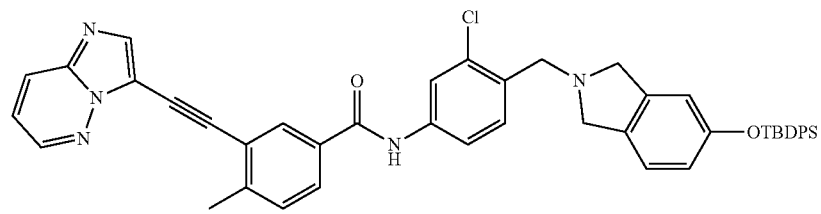

N-(4-((5-(((tert-butyldiphenylsilyl)oxy)isoindolin-2-yl)methyl)-3-chlorophenyl)-3-(imidazo[1,2-b]pyridazin-3-ylethynyl)-4-methyl benzamide (ZD-3-180) A 25-mL round-bottom flask was charged with tert-butyl-isoindolin-5-yloxy-diphenyl-silane (378 mg, 1.01 mmol) followed by N-[3-chloro-4-(chloromethyl)phenyl]-3-(2-imidazo[1,2-b]pyridazin-3-ylethynyl)-4-methyl-benzamide (220 mg, 0.51 mmol) and anhydrous DMF (4 mL) to give a dark brown solution. Lastly, N,N-diisopropylethylamine (0.2 mL, 1.16 mmol) and potassium iodide (16 mg, 0.1 mmol) were added, and the reaction stirred at ambient temperature overnight. The next morning, LCMS showed ~89% conversion of the starting chloride to the desired product [M+1]=772.2 and ~7% conversion to the doubly alkylated side product. The reaction was quenched with water and extracted out of brine solution with ethyl acetate (3×). Organics were dried over sodium sulfate, filtered, concentrated, and purified via flash column (0-20% MeOH in DCM). Fractions of interest were collected and concentrated to yield N-[4-[[5-[tert-butyl(diphenyl)silyl]oxyisoindolin-2-yl]methyl]-3-chloro-phenyl]-3-(2-imidazo[1,2-b]pyridazin-3-ylethynyl)-4-methyl-benzamide as a brown solid (278 mg, 71% yield); $^1$H NMR (500 MHz, CDCl$_3$) δ 8.49 (dd, J=4.4, 1.7 Hz, 1H), 8.09 (s, 1H), 8.04 (d, J=2.0 Hz, 1H), 8.00 (dd, J=9.2, 1.6 Hz, 1H), 7.96 (s, 1H), 7.83 (s, 1H), 7.81 (dd, J=8.0, 1.9 Hz, 1H), 7.72-7.70 (m, 4H), 7.50 (d, J=1.1 Hz, 2H), 7.43-7.34 (m, 8H), 7.14 (dd, J=9.2, 4.5 Hz, 1H), 6.88 (d, J=8.2 Hz, 1H), 6.62 (d, J=2.3

LCMS showed complete deprotection. The reaction was diluted with DCM and water and extracted with DCM (3×). The product was twice purified via silica gel flash chromatography (0-15% MeOH in DCM) to afford the product as a brown solid (28 mg; 41% yield); $^1$H NMR (600 MHz, d$_6$-acetone) δ 9.78 (s, 1H), 8.63 (dd, J=4.4, 1.5 Hz, 1H), 8.18 (d, J=1.9 Hz, 1H), 8.11 (td, J=4.2, 1.6 Hz, 3H), 7.96 (dd, J=7.9, 1.9 Hz, 1H), 7.77 (dd, J=8.4, 2.2 Hz, 1H), 7.56 (d, J=8.4 Hz, 1H), 7.48 (d, J=8.0 Hz, 1H), 7.35 (dd, J=9.2, 4.4 Hz, 1H), 7.01 (d, J=8.1 Hz, 1H), 6.71 (d, J=1.9 Hz, 1H), 6.67 (dd, J=8.1, 2.3 Hz, 1H), 3.97 (s, 2H), 3.87 (d, J=14.5 Hz, 4H), 2.63 (s, 3H) ppm; $^{13}$C NMR (150 MHz, d$_6$-acetone) δ 165.5, 157.5, 145.5, 144.7, 142.7, 140.9, 140.2, 139.1, 134.3, 133.8, 133.0, 131.9, 131.7, 131.1, 130.9, 129.0, 126.8, 123.6, 123.5, 121.5, 119.53, 119.47, 114.5, 113.5, 110.2, 97.3, 82.0, 59.8, 59.1, 57.0, 21.0 ppm; HRMS (APCI+) m/z: [M+H]$^+$ calcd for C$_{31}$H$_{25}$ClN$_5$O$_2$ 534.16913, found 534.16941.

Biological Assays

Compounds were tested against the Abl1 target kinase and showed potencies between 0.30 and 0.64 nanomolar, compared to nilotinib which showed a potency of 5.15 nanomolar in the same assay. When compared to nilotinib, key compounds showed similar c-Abl potency (~10 nM vs ~6 nM) and markedly improved hERG potency, with an exemplary compound showing greater than 22-fold decrease in off-target potency.

Summary of Results for Exemplary Compounds of the Present Disclosure

| Compound ID | Abl1 IC$_{50}$ (nM) | hERG IC$_{50}$ (mM) | SI | CYP3A4 IC$_{50}$ (mM) ‡ | CYP2D6 IC$_{50}$ (mM)‡ |
|---|---|---|---|---|---|
| TK3-141 | 0.30 | 0.345 | 1158 | 8.01 | 1.02 |
| TK3-144 | 0.39 | 0.103 | 263 | 11.75 | 1.99 |
| CD-1-002 | 0.64 | 0.081 | 126 | 12.82 | 24.8 |
| CD-1-051 | 9.93 | 5.02 | 506 | 5.57 | 30.0 |
| ZD-3-167 | 10.6 | >10 | >943 | 7.28 | 13.7 |
| CD-1-067 | >30 | 0.78 | <26 | 4.61 | 3.39 |
| Nilotinib | 5.91 | 0.45 | 76 | 0.58 | >100 |

Kinase Profiling

Figure 6:
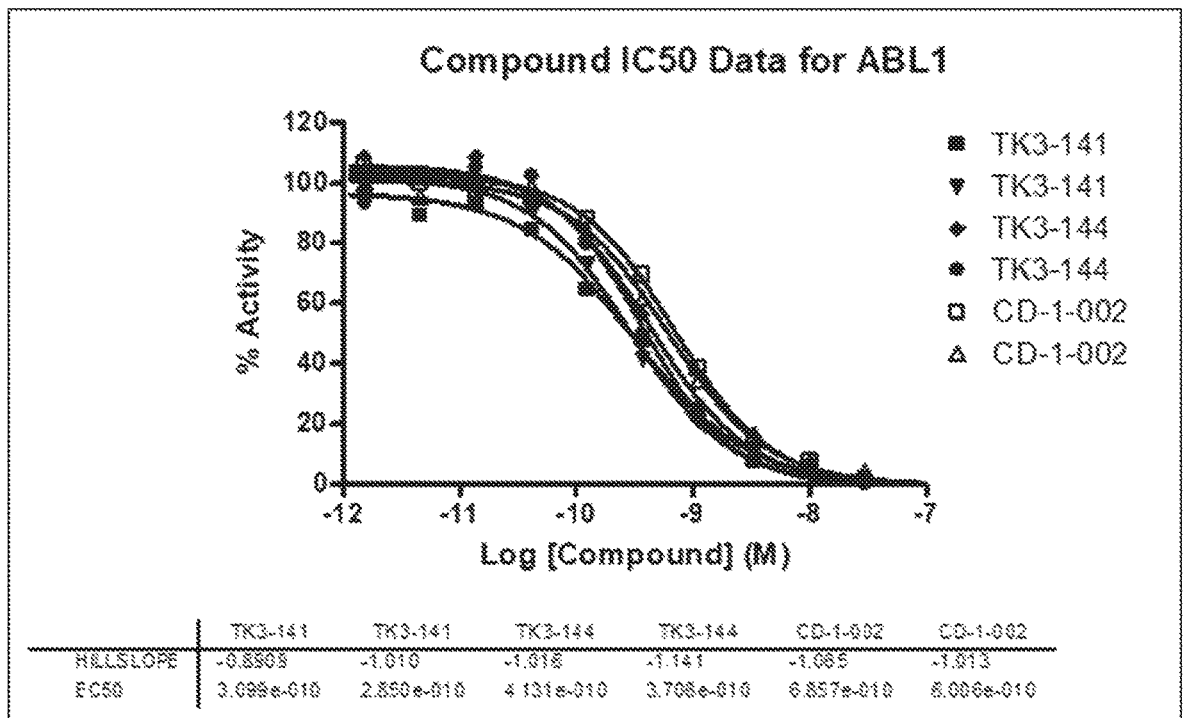
FIG. 6 shows ABL1 $IC_{50}$ data for exemplary compounds TK3-141, TK3-144 and CD-1-002.
Figure 7:
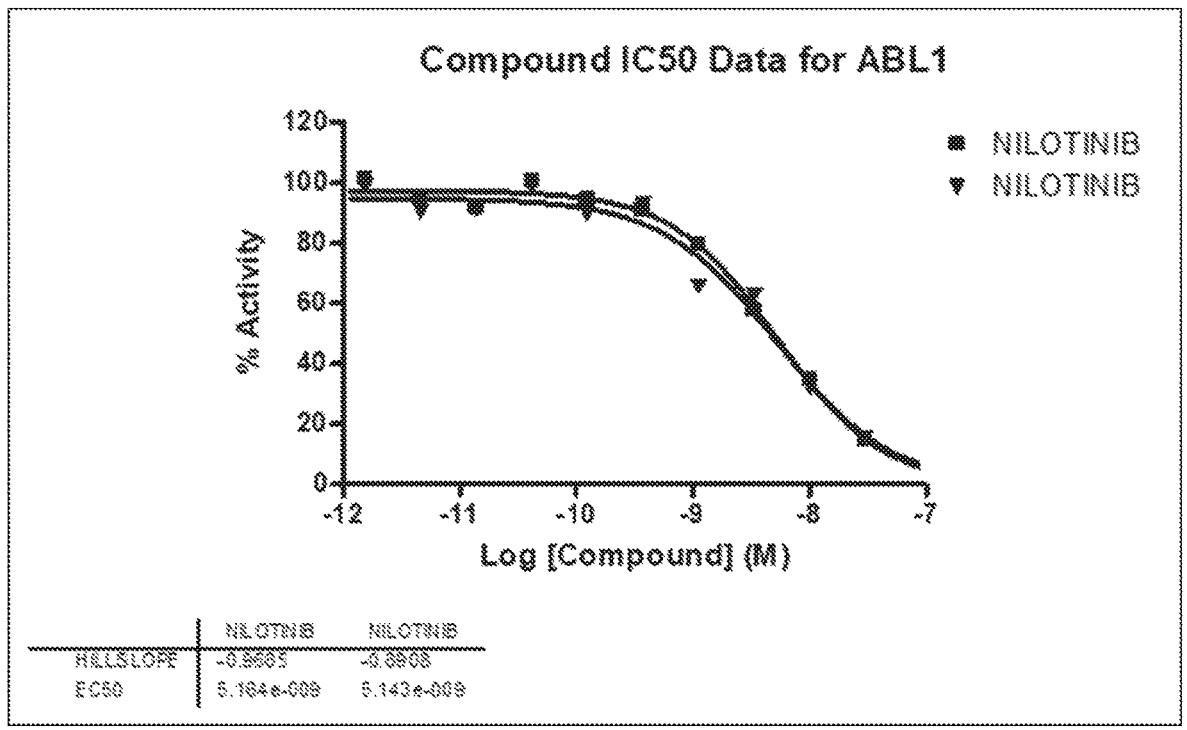
FIG. 7 shows ABL 1 $IC_{50}$ data for nilotinib (used as a control for the exemplary compounds listed in FIG. 6).
Figure 8:
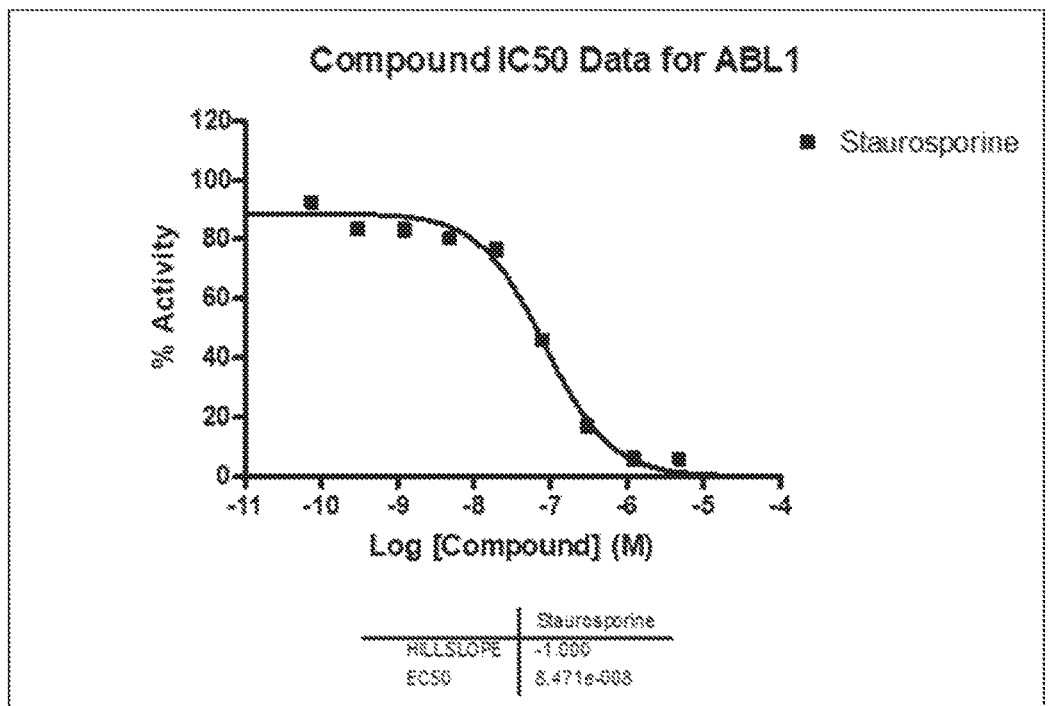
FIG. 8 shows ABL1 $IC_{50}$ data for staurosporine (used as a control for the exemplary compounds listed in FIG. 6).
Figure 9:
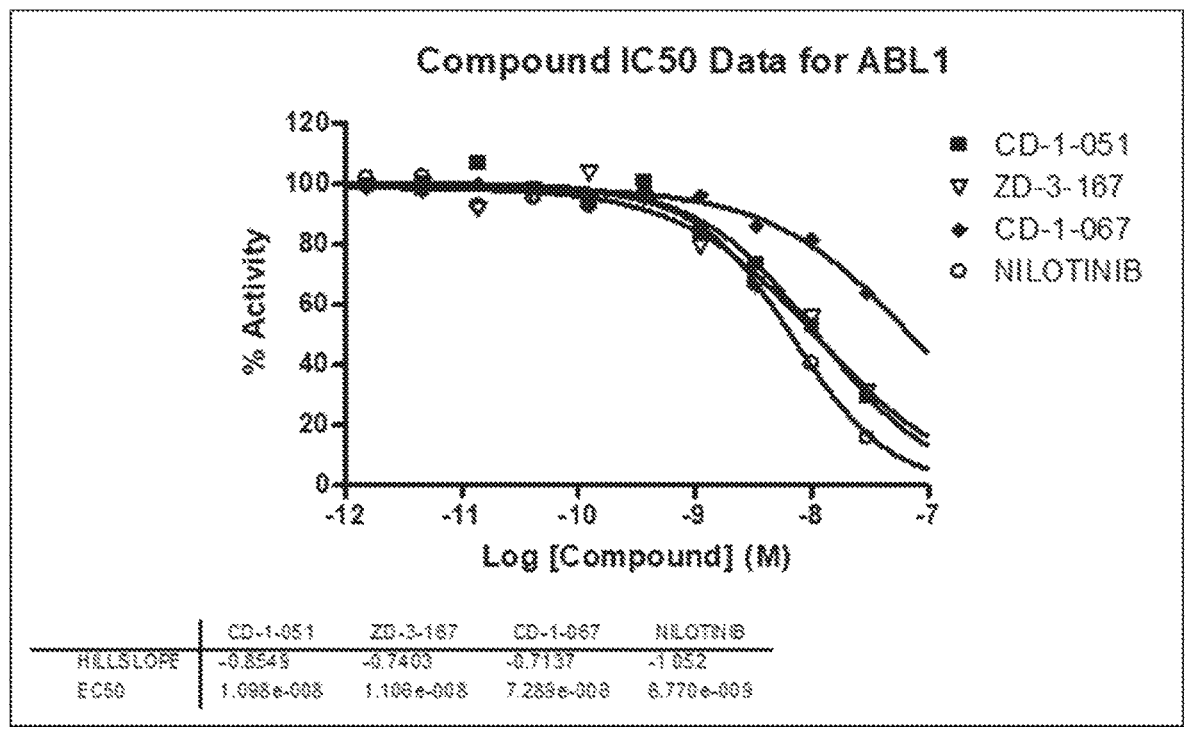
FIG. 9 shows ABL1 $IC_{50}$ data for exemplary compounds CD-1-051, ZD-3-167 and CD-1-067.
Figure 10:
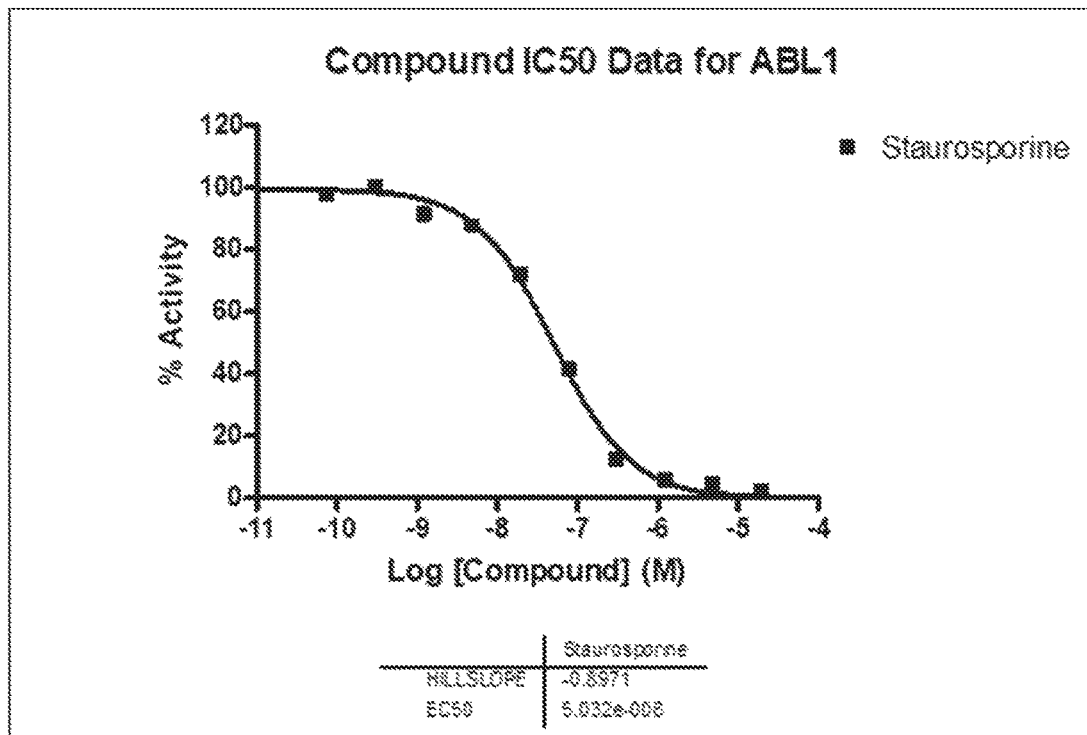
FIG. 10 shows ABL1 $IC_{50}$ data for staurosporine (used as a control for the exemplary compounds listed in FIG. 9).
Figure 11:
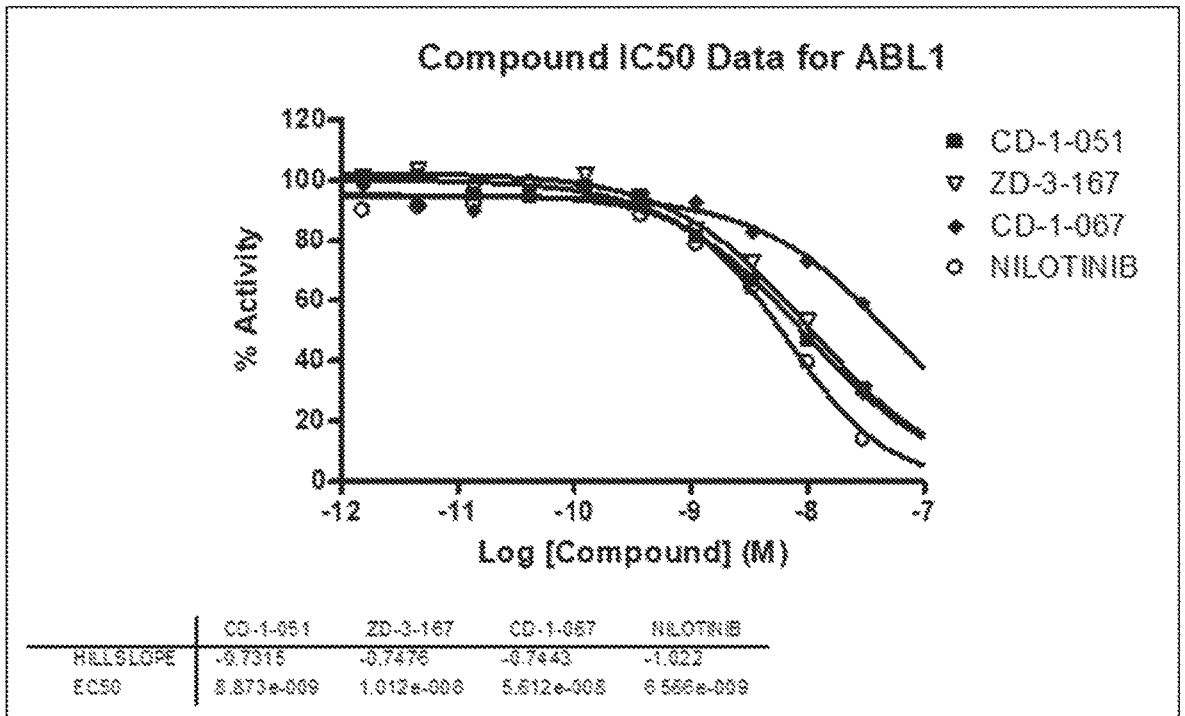
FIG. 11 shows further ABL1 $IC_{50}$ data for CD-1-051, ZD-3-167 and CD-1-067.
Figure 12:
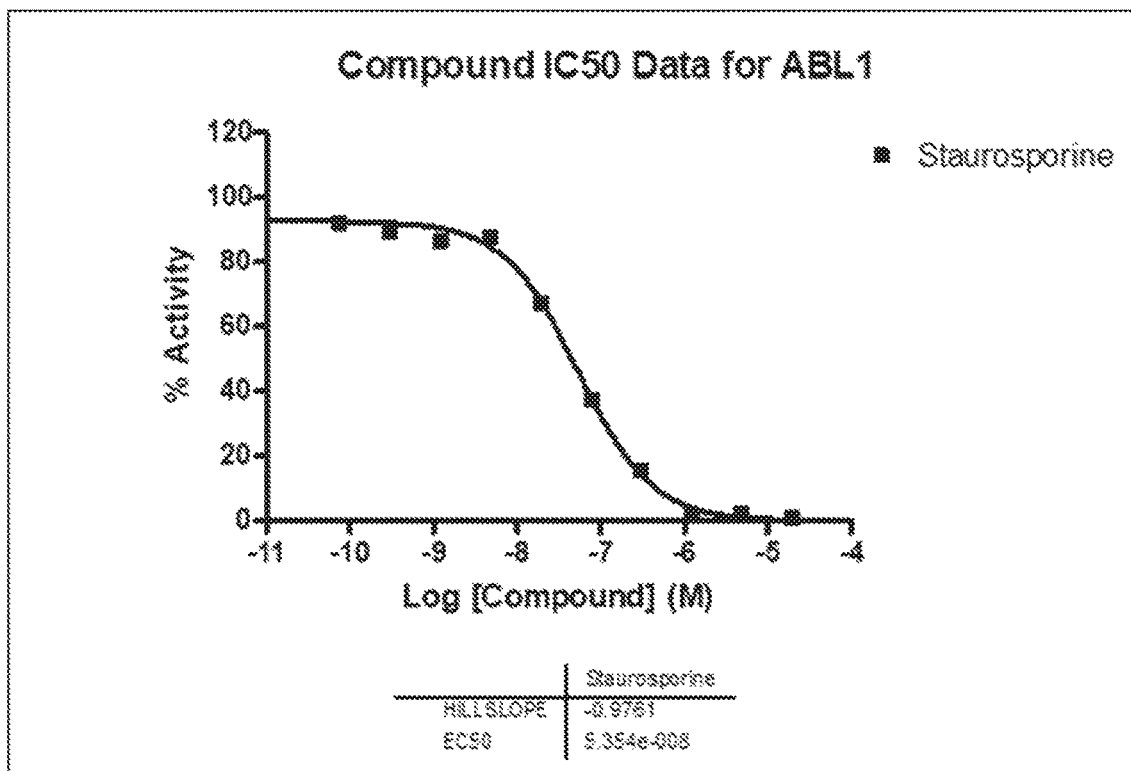
FIG. 12 shows ABL1 $IC_{50}$ data for staurosporine (used as a control for the exemplary compounds listed in FIG. 9).

Compounds were tested in 10-dose IC$_{50}$ mode in duplicate with 3-fold serial dilution starting at 30 µM. Control Compound Staurosporine was tested in 10-dose IC$_{50}$ mode with 4-fold serial dilution starting at 20 µM. Reactions were carried out at 10 µM ATP Curve fits were performed where the enzyme activities at the highest concentration of compounds were less than 65% (as shown in FIGS. 6,7 and 8 for exemplary compounds TK3-141, TK3-144 and CD-1-002 and FIGS. 9, 10, 11 and 12 for exemplary compounds CD-1-151, ZA-3-167 and CD-1-067).

IC$_{50}$ Summary:

| Compound ID: | Compound IC50* (M): ABL1 | | |
|---|---|---|---|
| | Data 1 | Data 2 | Avg |
| TK3-141 | 3.10E−10 | 2.85E−10 | 2.97E−10 |
| TK3-144 | 4.13E−10 | 3.71E−10 | 3.92E−10 |
| CD-1-002 | 6.86E−10 | 6.01E−10 | 6.43E−10 |
| Nilotinib | 5.16E−09 | 5.14E−09 | 5.15E−09 |
| Staurosporine | 8.47E−08 | | |

| Compound ID: | Compound IC50* (M): ABL1 | | | Average hERG (IC50) | Selectivity Ratio |
|---|---|---|---|---|---|
| | Data 1 | Data 2 | Avg | | |
| CD-1-051 | 1.10E−08 | 8.87E−09 | 9.93E−09 | 5.02E−06 | 505.72 |
| ZD-3-167 | 1.11E−08 | 1.01E−08 | 1.06E−08 | 1.02E−05 | 9.63E+02 |
| CD-1-067 | >3.00E−08 | >3.00E−08 | | | |
| Nilotinib | 6.77E−09 | 6.57E−09 | 6.67E−09 | 2.92E−07 | 43.79 |
| Staurosporine | 5.03E−08 | 5.35E−08 | | | | hERG Profiling

Compounds were prepared as 10 mM DMSO stock and stored at −80° C. Compounds were tested in a 10-dose IC$_{50}$ duplicate mode with a 3-fold serial dilution starting at 10 uM. Control compounds, Nilotinib and Lapatinib, were tested in a 10-dose IC$_{50}$ with 3-fold serial dilution starting at 10 uM. Control compound, E-4031, was tested in a 10-dose IC$_{50}$ with 3-fold serial dilution starting at 1 uM.

Assay Format: The assay is based on the competition of fluorescently labeled Tracer binding to the membrane preparation containing hERG.

Assay conditions: 1 nM Predictor™ hERG Tracer Red; 1X Predictor™ hERG Membrane

Assay Buffer: 25 mM Hepes, pH 7.5, 15 mM KCl, 1 mM MgCl2, 0.05% PF-127, and 1% DMSO Assay Procedure: Compounds in DMSO were added into the Membrane mixture by using Acoustic Technology. Tracer was added, and gentled mixed in the dark. FP was measured after 4 hours incubation at room temperature and mP calculated.

Measurement: Ex=531 nm FP, Em=595 nm P and S

Figure 13:
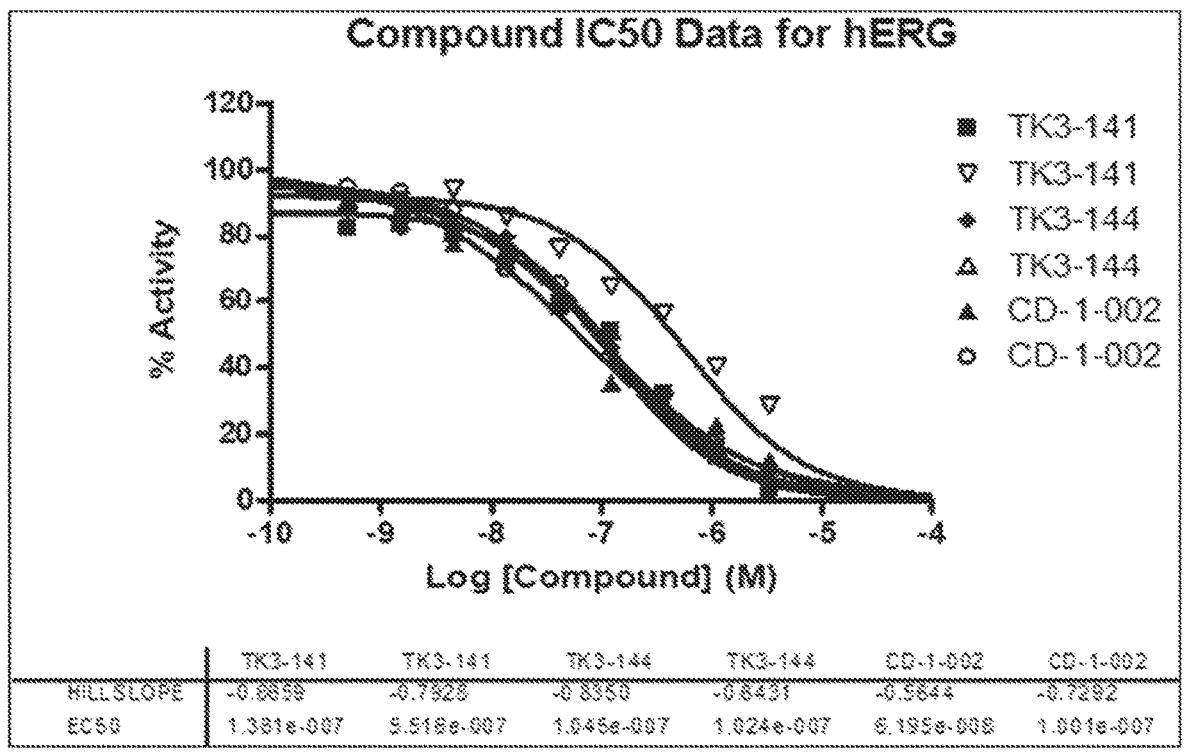
FIG. 13 shows hERG $IC_{50}$ data for exemplary compounds TK3-141, TK3-144 and CD-1-002.
Figure 14:
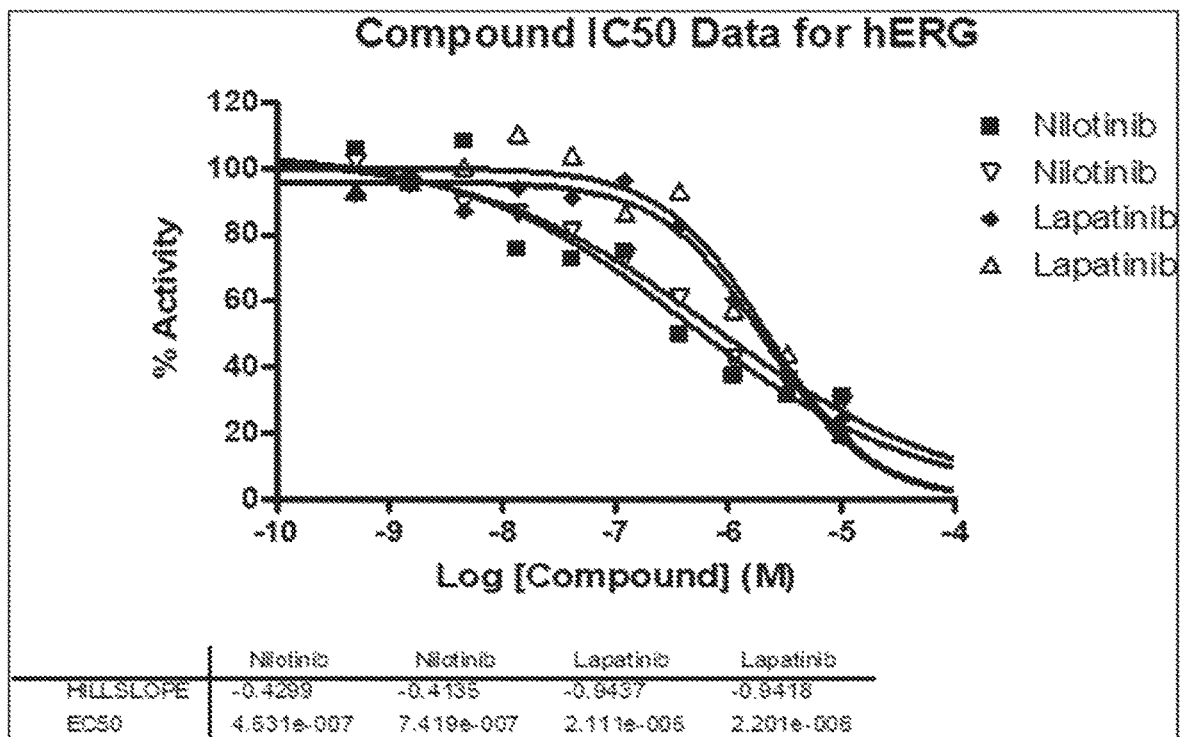
FIG. 14 shows hERG $IC_{50}$ data for nilotinib (used as a control for the exemplary compounds listed in FIG. 13).
Figure 15:
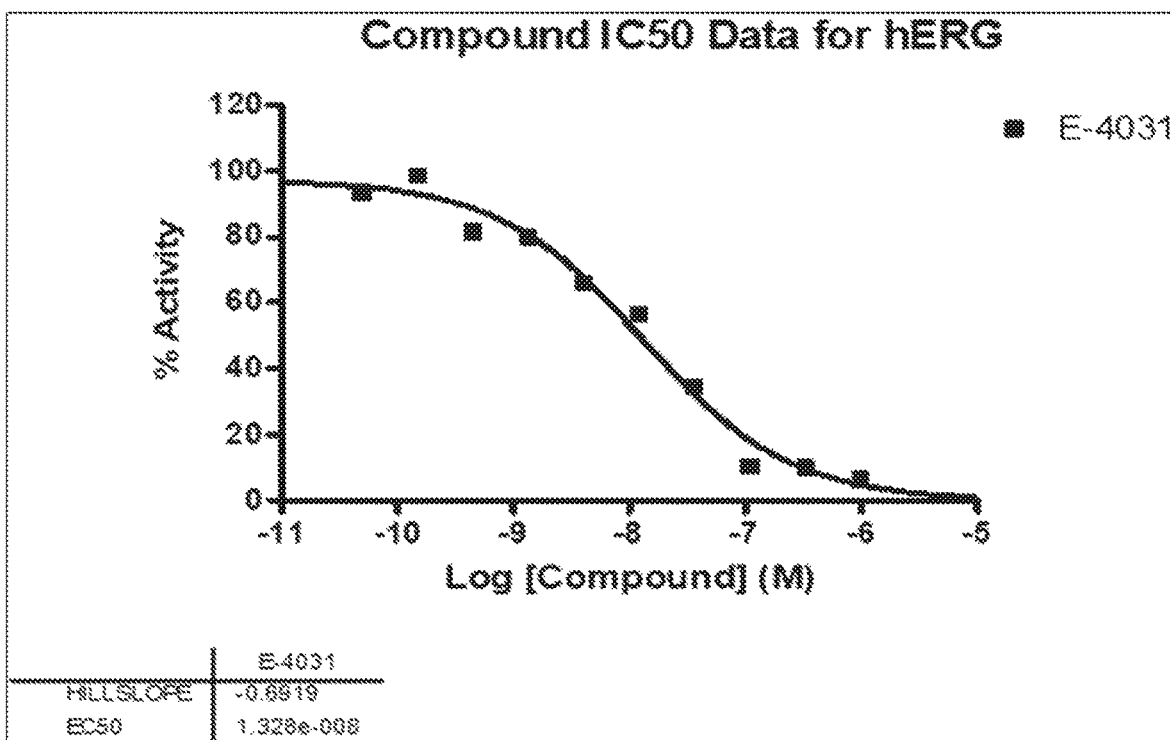
FIG. 15 shows hERG $IC_{50}$ data for E-403 (used as a control for the exemplary compounds listed in FIG. 13).
Figure 16:
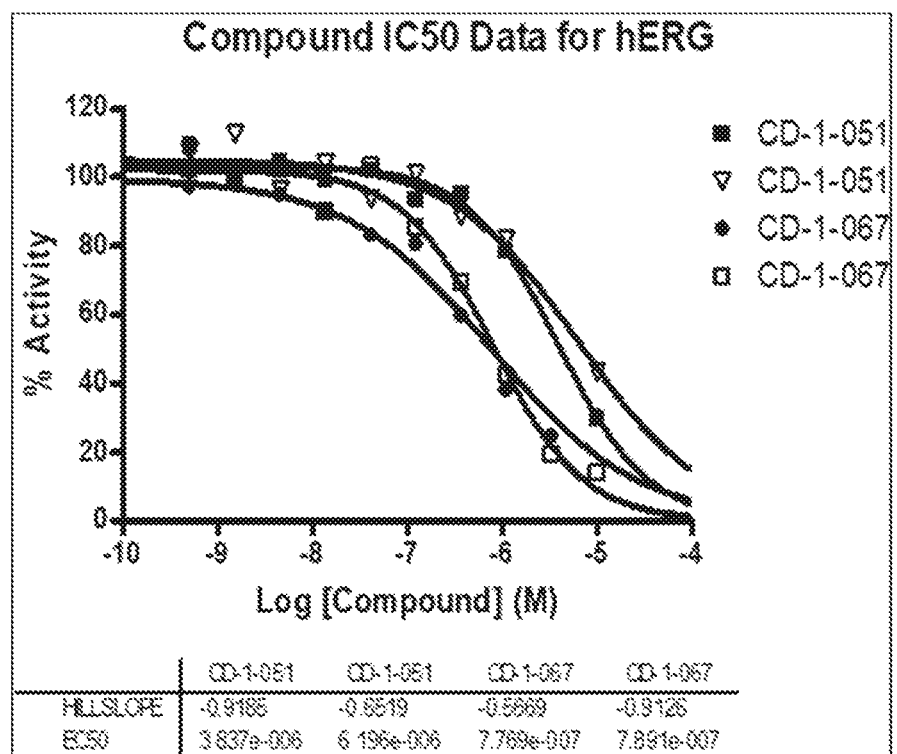
FIG. 16 shows hERG $IC_{50}$ data for exemplary compounds CD-1-051 and CD-1-067.
Figure 17:
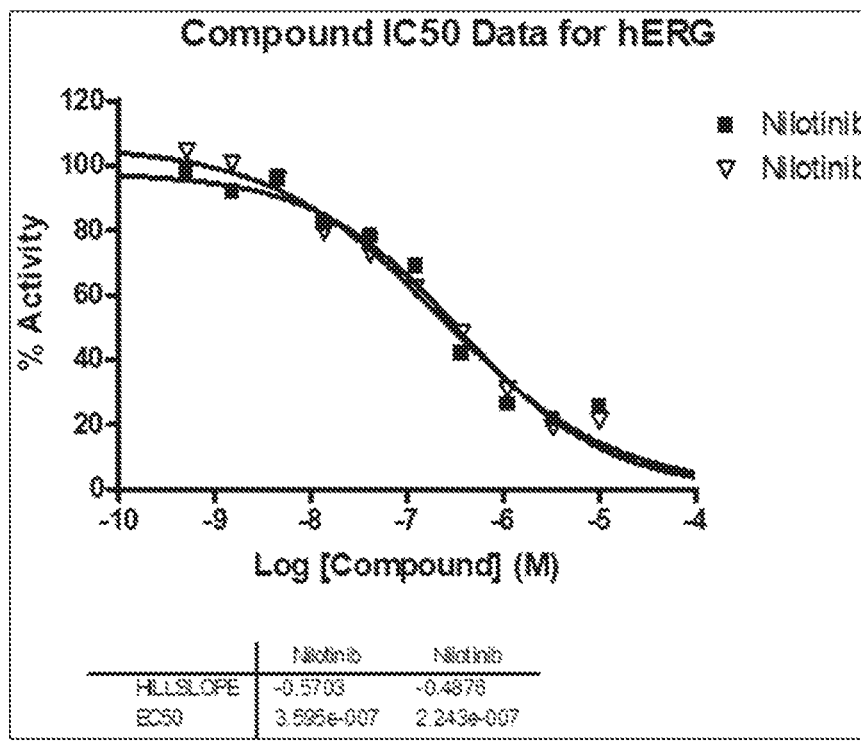
FIG. 17 shows hERG $IC_{50}$ data for nilotinib (used as a control for the exemplary compounds listed in FIG. 16).
Figure 18:
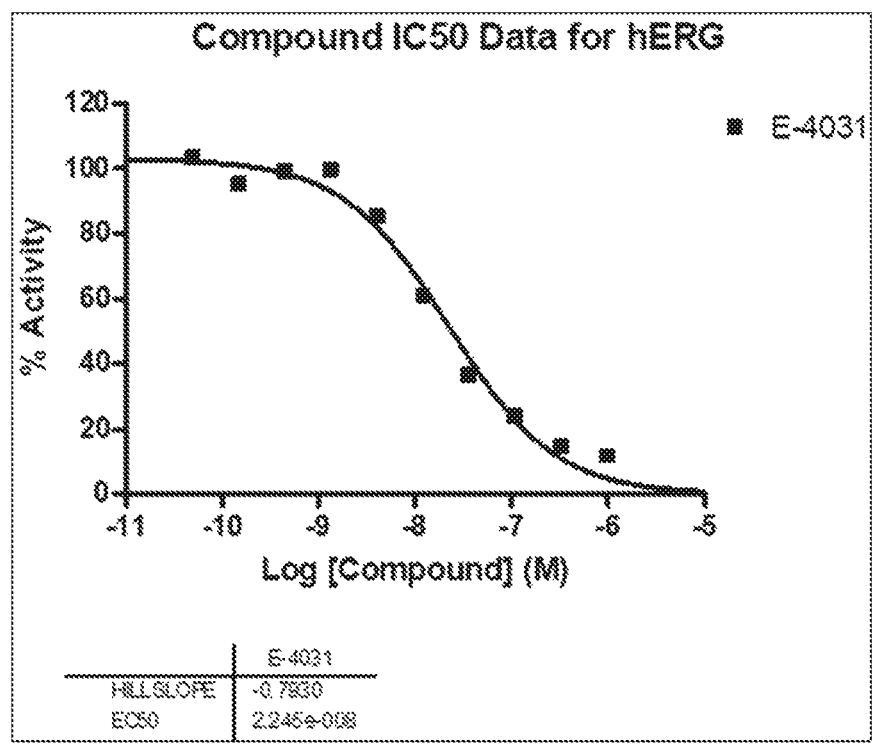
FIG. 18 shows hERG $IC_{50}$ data for E-4031 (used as a control for the exemplary compounds listed in FIG. 16).

Curve fits were performed by GraphPad Prism software when the activities at the highest concentration of compounds were less than 65%. and*Background was established by the average FP signal in the presence of 30 uM E-4031 (See FIGS. 13, 14, and 15 for exemplary compounds TK3-141, TK3-144 and CD-1-002 and the controls Nilotinib and E-4031 and FIGS. 16, 17 and 18 for compounds CD-1-051 and CD-1-67 and the controls Nilotinib and E-4031).

Summary Tables for hERG:

| Compound ID: | IC$_{50}$ of Tracer Binding (M) hERG | | |
|---|---|---|---|
| | Data 1 | Data 2 | AVERAGE |
| TK3-141 | 1.38E−07 | 5.52E−07 | 3.45E−07 |
| TK3-144 | 1.05E−07 | 1.02E−07 | 1.03E−07 |
| CD-1-002 | 6.20E−08 | 1.00E−07 | 8.10E−08 |
| Nilotinib | 4.63E−07 | 7.42E−07 | 6.03E−07 |
| E-4031 | 1.33E−08 | | |

| Compound ID: | IC$_{50}$ of Tracer Binding (M) hERG | |
|---|---|---|
| | Data 1 | Data 2 |
| CD-1-051 | 3.84E−06 | 6.20E−06 |
| ZD-3-167 | * | * |
| CD-1-067 | 7.77E−07 | 7.89E−07 |
| Nilotinib | 3.60E−07 | 2.24E−07 |
| E-4031 | 2.25E−08 | |

* Inhibition > 10 µM, compound activity could not be fit to an IC$_{50}$ curve.

The invention claimed is:

1. A compound N-(3-chloro-4-((5-hydroxyisoindolin-2-yl)methyl)phenyl)-3-(imidazo[1,2-b]pyridazin-3-ylethynyl)-4-methylbenzamide or a salt thereof.

2. A pharmaceutical composition, comprising the compound of claim 1 and a pharmaceutically acceptable excipient.

3. The pharmaceutical composition of claim 2, in the form of tablet, capsule, pill, gel, or granule.

4. A compound N-[3-chloro-4-(1,4,5,7-tetrahydropyrazolo[3,4-c]pyridin-6-ylmethyl)phenyl]-3-(2-imidazo[1,2-b]pyridazin-3-ylethynyl)-4-methyl-benzamide or a salt thereof.

5. A pharmaceutical composition, comprising the compound of claim 4 and a pharmaceutically acceptable excipient.

6. The pharmaceutical composition of claim 5, in the form of tablet, capsule, pill, gel, or granule.

7. A compound N-[3-chloro-4-(4,6-dihydro-1H-pyrrolo[3,4-c]pyrazol-5-ylmethyl)phenyl]-3-(2-imidazo[1,2-b]pyridazin-3-ylethynyl)-4-methyl-benzamide or a salt thereof.

8. A pharmaceutical composition, comprising the compound of claim 7 and a pharmaceutically acceptable excipient.

9. The pharmaceutical composition of claim 8, in the form of tablet, capsule, pill, gel, or granule.

10. A compound N-[3-cyclopropyl-4-[[4-(2-methoxyethyl)piperazin-1-yl]methyl]phenyl]-3-(2-imidazo[1,2-b]pyridazin-3-ylethynyl)-4-methyl-benzamide or a salt thereof.

11. A pharmaceutical composition, comprising the compound of claim 10 and a pharmaceutically acceptable excipient.

12. The pharmaceutical composition of claim 11, in the form of tablet, capsule, pill, gel, or granule.

* * * * *